(12) United States Patent
Kaehr

(10) Patent No.: US 10,947,349 B2
(45) Date of Patent: Mar. 16, 2021

(54) SHAPE-PRESERVING POLYMERIC REPLICATION OF BIOLOGICAL MATTER

(71) Applicant: National Technology & Engineering Solutions of Sandia, LLC, Albuquerque, NM (US)

(72) Inventor: Bryan James Kaehr, Albuquerque, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 0 days.

(21) Appl. No.: 16/711,150

(22) Filed: Dec. 11, 2019

(65) Prior Publication Data
US 2020/0115507 A1  Apr. 16, 2020

Related U.S. Application Data

(62) Division of application No. 15/282,511, filed on Sep. 30, 2016, now Pat. No. 10,538,632.

(51) Int. Cl.
| C08G 83/00 | (2006.01) |
| A61K 49/00 | (2006.01) |
| A61K 31/80 | (2006.01) |

(52) U.S. Cl.
CPC .......... C08G 83/001 (2013.01); A61K 31/80 (2013.01); A61K 49/00 (2013.01)

(58) Field of Classification Search
CPC ....... C08G 83/001; A61K 31/80; A61K 49/00
See application file for complete search history.

(56) References Cited

U.S. PATENT DOCUMENTS

| | | |
|---|---|---|
| 5,078,919 A | 1/1992 | Ashley et al. |
| 5,122,305 A | 6/1992 | Ashley et al. |
| 5,137,659 A | 8/1992 | Ashley et al. |
| 5,151,110 A | 9/1992 | Bein et al. |
| 5,224,972 A | 7/1993 | Frye et al. |
| 5,240,647 A | 8/1993 | Ashley et al. |
| 5,306,445 A | 4/1994 | Reed et al. |
| 5,313,485 A | 5/1994 | Hamil et al. |
| 5,565,142 A | 10/1996 | Deshpande et al. |
| 5,589,396 A | 12/1996 | Frye et al. |
| 5,770,275 A | 6/1998 | Raman et al. |
| 5,772,735 A | 6/1998 | Sehgal et al. |
| 5,858,457 A | 1/1999 | Brinker et al. |
| 5,935,646 A | 8/1999 | Raman et al. |
| 5,948,482 A | 9/1999 | Brinker et al. |
| 5,949,071 A | 9/1999 | Ruffner et al. |
| 6,057,377 A | 5/2000 | Sasaki et al. |
| 6,258,305 B1 | 7/2001 | Brinker et al. |
| 6,264,741 B1 | 7/2001 | Brinker et al. |
| 6,270,846 B1 | 8/2001 | Brinker et al. |
| 6,387,453 B1 | 5/2002 | Brinker et al. |
| 6,471,761 B2 | 10/2002 | Fan et al. |
| 6,495,352 B1 | 12/2002 | Brinker et al. |
| 6,536,604 B1 | 3/2003 | Brinker et al. |
| 6,808,867 B2 | 10/2004 | Doshi et al. |
| 6,913,832 B2 | 7/2005 | Fan et al. |
| 6,983,093 B2 | 1/2006 | Fraval et al. |
| 7,332,264 B2 | 2/2008 | Doshi et al. |
| 7,485,343 B1 | 2/2009 | Branson et al. |
| 7,744,673 B2 | 6/2010 | Jiang et al. |
| RE41,612 E | 8/2010 | Brinker et al. |
| 7,947,579 B2 | 5/2011 | Jiang et al. |
| 8,092,595 B1 | 1/2012 | Fan et al. |
| 8,187,678 B2 | 5/2012 | Jiang et al. |
| 8,246,933 B2 | 8/2012 | Jiang et al. |
| 8,318,127 B1 | 11/2012 | Jiang et al. |
| 8,501,057 B1 | 8/2013 | Jiang et al. |
| 8,663,742 B2 | 3/2014 | Kissel et al. |
| 8,734,816 B2 | 5/2014 | Liu et al. |
| 8,859,190 B1 | 10/2014 | Dirk et al. |
| 9,273,305 B1 | 3/2016 | Kaehr et al. |
| 9,970,000 B2 | 5/2018 | Kaehr et al. |
| 9,989,447 B1 | 6/2018 | Kaehr et al. |
| 10,214,833 B1 | 2/2019 | Kaehr et al. |
| 2010/0055733 A1 | 3/2010 | Lutolf et al. |
| 2011/0186971 A1 | 8/2011 | Jiang et al. |
| 2012/0040577 A1 | 2/2012 | Kissel et al. |
| 2015/0144490 A1 | 5/2015 | Deisseroth et al. |

FOREIGN PATENT DOCUMENTS

| | | |
|---|---|---|
| WO | WO 03/016040 A1 | 2/2003 |
| WO | WO 2008/060883 A2 | 5/2008 |
| WO | WO 2011/011468 A2 | 1/2011 |

OTHER PUBLICATIONS

Chemburu et all, Molecules 2010, 15, 1932-1957 (Year: 2010).*
U.S. Appl. No. 15/217,606, filed Jul. 22, 2016, Kaehr et al.
Alemán J et al., "Definitions of terms relating to the structure and processing of sols, gels, networks, and inorganic-organic hybrid materials (IUPAC Recommendations 2007)," *Pure Appl. Chem.* 2007;79(10):1801-29.
Antonelli DM et al., "Synthesis of hexagonally packed mesoporous $TiO_2$ by a modified sol-gel method," *Angew. Chem. Int. Ed. Engl.* 1995;34:2014-7.
Avnir D et al., "Recent bio-applications of sol-gel materials," *J. Mater. Chem.* 2006;16:1013-30.

(Continued)

*Primary Examiner* — Robert S Cabral

(74) *Attorney, Agent, or Firm* — Helen S. Baca; Kevin W. Bieg

(57) ABSTRACT

The present invention relates to a method of forming silica nanolayers on or within a biological sample, thereby capturing structural details that are present in the sample. The resultant silica composite or silica replica, in turn, can be employed as a template for a replica having those structural details captured in a polymer. Also provided herein are synthetic constructs including a polymeric replica, which can have any useful feature (e.g., oxygen-binding capacity).

15 Claims, 9 Drawing Sheets

(56) References Cited

OTHER PUBLICATIONS

Baca HK et al., "Cell-directed assembly of bio/nano interfaces—A new scheme for cell immobilization," *Acc. Chem. Res.* Sep. 2007;40(9):836-45.
Baca HK et al., "Cell-directed assembly of lipid-silica nanostructures providing extended cell viability," *Science* Jul. 21, 2006;313(5785):337-41.
Baca HK et al., "Cell-directed-assembly: Directing the formation of nano/bio interfaces and architectures with living cells," *Biochim. Biophys. Acta* Mar. 2011;1810(3):259-67.
Bao Z et al., "Chemical reduction of three-dimensional silica micro-assemblies into microporous silicon replicas," *Nature* Mar. 2007;446:172-5.
Bassindale et al., "Simple and mild preparation of silica-enzyme composites from silicic acid solution," *J. Mater. Chem.* 2009;19:7606-9.
Beck JS et al., "A new family of mesoporous molecular sieves prepared with liquid crystal templates," *J. Am. Chem. Soc.* 1992;114(27):10834-43.
Betancor L et al., "Bioinspired enzyme encapsulation for biocatalysis," *Trends Biotechnol.* Aug. 2008;26(10):566-72.
Boissiere C et al., "Aerosol route to functional nanostructured inorganic and hybrid porous materials," *Adv. Mater.* 2011;23:599-623.
Borges J et al., "Molecular interactions driving the layer-by-layer assembly of multilayers," *Chem. Rev.* 2014;114:8883-942.
Braet F et al., "Drying cells for SEM, AFM and TEM by hexamethyldisilazane: A study on hepatic endothelial cells," *J. Microsc.* Apr. 1997;186(1):84-7.
Bray DF et al., "Comparison of hexamethyldisilazane (HMDS), Peldri II and critical-point drying methods for scanning electron microscopy of biological specimens," *Microsc. Res. Tech.* 1993;26:489-95.
Brinker CJ et al., "Evaporation-induced self-assembly: Nanostructures made easy," *Adv. Mater.* May 1999;11(7):579-85.
Brott LL et al., "Ultrafast holographic nanopatterning of biocatalytically formed silica," *Nature* Sep. 2001;413(6853):291-3.
Browning N et al., "Recent developments in dynamic transmission electron microscopy," *Curr. Opin. Solid State Mater. Sci.* Feb. 2012;16(1):23-30.
Brunner E et al., "Chitin-based organic networks: an integral part of cell wall biosilica in the diatom Thalassiosira pseudonana," *Angew. Chem. Int. Ed. Engl.* 2009;48:9724-7.
Brunon A et al., "Mechanical characterization of liver capsule through uniaxial quasi-static tensile tests until failure," *J. Biomech.* 2010;43:2221-7.
Bushby AJ et al., "Imaging three-dimensional tissue architectures by focused ion beam scanning electron microscopy," *Nat. Protoc.* Jun. 2011;6(6):845-58 (abstract only).
Campbell NA, Reece JB, Mitchell LG (eds.), "Traffic across membranes," in *Biology* (Fifth edition), 1999, Benjamin/Cummings, Menlo Park, CA, pp. 136-139.
Carroll NJ et al., "Microparticles with bimodal nanoporosity derived by microemulsion templating," *Langmuir* 2009;25(23):13540-4.
Cha JN et al., "Silicatein filaments and subunits from a marine sponge direct the polymerization of silica and silicones in vitro," *Proc. Nat'l Acad. Sci. USA* Jan. 1999;96:361-5.
Chen CL et al., "Peptide-based methods for the preparation of nanostructured inorganic materials," *Angew. Chem. Int. Ed. Engl.* Mar. 8, 2010;49(11):1924-42.
Chen K et al., "Low modulus biomimetic microgel particles with high loading of hemoglobin," *Biomacromolecules* 2012;13:2748-59.
Chen LY et al., "Mass fabrication and delivery of 3D multilayer µTags into living cells," *Sci. Rep.* 2013;3:2295 (6 pp.).
Chen Z et al., "DNA translocation through an array of kinked nanopores," *Nat. Mater.* Aug. 2010;9(8):667-75.
Choi CH et al., "Controlled fabrication of microparticles with complex 3D geometries by tunable interfacial deformation of confined polymeric fluids in 2D micromolds," *ACS Appl. Mater. Interfaces* 2015;7:11393-401.
Chung K et al., "Structural and molecular interrogation of intact biological systems," *Nature* 2013;497:332-337 with Supplementary methods (2 pp.).
Coradin T et al., "Interactions of bovine serum albumin and lysozyme with sodium silicate solutions," *Colloids Surf. B* 2003;29:189-96.
Cui J et al., "Mechanically tunable, self-adjuvanting nanoengineered polypeptide particles," *Adv. Mater.* 2013;25:3468-72.
Cui J et al., "Super-soft hydrogel particles with tunable elasticity in a microfluidic blood capillary model," *Adv. Mater.* 2014;26:7295-9.
Dahmen U et al., "Background, status and future of the transmission electron aberration-corrected microscope project," *Phil. Trans. R. Soc. A* 2009;367:3795-808.
De Jonge N et al., "Electron microscopy of specimens in liquid," *Nat. Nanotechnol.* 2011;695-704.
Dendukuri D et al., "Continuous-flow lithography for high-throughput microparticle synthesis," *Nat. Mater.* May 2006;5(5):365-9.
Dengler EC et al., "Mesoporous silica-supported lipid bilayers (protocells) for DNA cargo delivery to the spinal cord," *J. Control. Release* Jun. 10, 2013;168(2):209-24.
Denk W et al., "Serial block-face scanning electron microscopy to reconstruct three-dimensional tissue nanostructure," *PLoS Biol.* Nov. 2004;2(11):1900-9.
Dickerson MB et al., "Protein- and peptide-directed syntheses of inorganic materials," *Chem. Rev.* 2008;108:4935-78.
Doshi N et al., "Red blood cell-mimicking synthetic biomaterial particles," *Proc. Nat'l Acad. Sci. USA* 2009;106(51):21495-9.
Fernandes FM et al., "Self-assembly in biosilification and biotemplated silica materials," *Nanomaterials* 2014;4:792-812.
Fratzl P et al., "Bio-inspired materials—Mining the old literature for new ideas," *Adv. Mater.* 2010;22:4547-50.
Frens G, "Controlled nucleation for the regulation of the particle size in monodisperse gold suspensions," *Nature* 1973;241:20-2.
Gautier C et al., "Biomimetic dual templating of silica by polysaccharide/protein assemblies," *Colloids Surf. B* 2008;65:140-5.
Geng Y et al., "Chloroquine-induced autophagic vacuole accumulation and cell death in glioma cells is p53 independent," *Neuro. Oncol.* May 2010;12(5):473-81.
Gilbert TW et al., "Decellularlization of tissues and organs," Biomaterials Jul. 2006;27(19):3675-83.
Glotzer SC et al., "Anisotropy of building blocks and their assembly into complex structures," *Nat. Mater.* Aug. 2007;6(8):557-62.
Goodwin WB et al., "Conversion of pollen particles into three-dimensional ceramic replicas tailored for multimodal adhesion," *Chem. Mater.* 2013;25(22):4529-36.
Haghgooie R et al., "Squishy non-spherical hydrogel microparticles," *Macromol. Rapid Commun.* 2010;31:128-34.
Hall A, "Rho GTPases and the actin cytoskeleton," *Science* Jan. 19998;279(5350):509-14.
Hanefeld U et al., "Understanding enzyme immobilisation," *Chem. Soc. Rev.* Feb. 2009;38(2):453-68.
Harper JC et al., "Biocompatible microfabrication of 3D isolation chambers for targeted confinement of individual cells and their progeny," *Anal. Chem.* Oct. 2012;84(21):8985-9.
Harper JC et al., "Cell-directed integration into three-dimensional lipid—Silica nanostructured matrices," *ACS Nano* Oct. 26, 2010;4(10):5539-50.
Harper JC et al., "Encapsulation of S. cerevisiae in poly(glycerol) silicate derived matrices: Effect of matrix additives and cell metabolic phase on long-term viability and rate of gene expression," *Chem. Mater.* Apr. 2011;23(10):2555-64.
Harper JC et al., "Orthogonal cell-based biosensing: Fluorescent, electrochemical, and colorimetric detection with silica-immobilized cellular communities integrated with an ITO-glass/plastic laminate cartridge," *Small* Sep. 10, 2012;8(17):2743-51.
Hatton B et al., "Assembly of large-area, highly ordered, crack-free inverse opal films," *Proc. Nat'l Acad. Sci. USA* 2010;107:10354-9.
Helgeson ME et al., "Hydrogel microparticles from lithographic processes: Novel materials for fundamental and applied colloidal science," *Curr. Opin. Colloid Interface Sci.* Apr. 2011;16(2):106-17.

(56) References Cited

OTHER PUBLICATIONS

Hildebrand M et al., "Application of AFM in understanding biomineral formation in diatoms," *Pflügers Arch.* 2008;456:127-37.
Hildebrand M, "Diatoms, biomineralization processes, and genomics," *Chem. Rev.* 2008;108:4855-74.
Hildebrand M, "Prospects of manipulating diatom silica nanostructure," *J. Nanosci. Nanotechnol.* 2005;5:146-57.
Holland BT et al., "Synthesis of macroporous minerals with highly ordered three-dimensional arrays of spheroidal voids," *Science* Jul. 1998;281:538-40.
Holzapfel GA et al., "Biomechanics of soft tissue," *Biomech Preprint Series*, paper No. 7, Graz University of Technology, Austria, Nov. 2000 (15 pp.).
Hu CMJ et al., "Erythrocyte membrane-camouflaged polymeric nanoparticles as a biomimetic delivery platform," *Proc. Nat'l Acad. Sci. USA* Jul. 2011;108(27):10980-5.
Hu CMJ et al., "Erythrocyte-inspired delivery systems," *Adv. Healthcare Mater.* Sep. 2012;1(5):537-47.
Hudson S et al., "Proteins in mesoporous silicates," *Angew. Chem. Int. Ed. Engl.* 2008;47:8582-94.
Huo Q et al., "Generalized synthesis of periodic surfactant/inorganic composite materials," *Nature* 1994;368:317-21.
Jiang X et al., "Aerosol fabrication of hollow mesoporous silica nanoparticles and encapsulation of L-methionine as a candidate drug cargo," *Chem. Commun. (Camb.)* May 7, 2010;46(17):3019-21.
Jiang X et al., "Aerosol-assisted synthesis of monodisperse single-crystalline a-cristobalite nanospheres," *Chem. Commun. (Camb.)* Jan. 30, 2012;48(9):1293-5.
Jiang X et al., "Hydrothermal synthesis of monodisperse single-crystalline alpha-quartz nanospheres," *Chem. Commun. (Camb.)* Jul. 14, 2011;47(26):7524-6.
Jiang X et al., "Photoresponsive release from azobenzene-modified single cubic crystal NaCl/silica particles," *J. Nanomater.* 2011; (6 pages).
Jiang Y et al., "Click hydrogels, microgels and nanogels: Emerging platforms for drug delivery and tissue engineering," *Biomaterials* 2014;35:4969-85.
Johnson P et al., "Nano-engineered, ultra stable, live cell vaccines against tuberculosis," 2011, 1 page (available from http://posterhall.org/system/igert/igert2011/posters/146/presentations/2011_IGERT_final_-_PJohnson.pdf?1302924782, last accessed Apr. 20, 2014).
Kaehr B et al., "Cellular complexity captured in durable silica biocomposites," *Proc. Nat'l Acad. Sci. USA* Oct. 23, 2012;109(43):17336-41.
Kaehr B et al., Supporting information for "Cellular complexity captured in durable silica biocomposites," *Proc. Nat'l Acad. Sci. USA* Oct. 23, 2012;109(43):17336-41, available at http://www.pnas.org/content/109/43/17336.long?tab=ds (last accessed May 1, 2014) (6 pp.).
Kaehr B, "Development and characterization of 3D, nano-confined multicellular constructs for advanced biohybrid devices," *Sandia Report SAND2011-6892*, Sep. 2011 (24 pp.).
Kaehr B, "Encoded cellular shapes for synthesis of non-spherical particles," presented at the 248th ACS National Meeting and Exposition, on Aug. 14, 2014 in San Francisco, CA (17 pp.).
Kemmenoe BH et al., "Structure-analysis of sputter-coated and ion-beam sputter-coated films: A comparative-study," *J. Microsc.* Nov. 1983;132(Pt 2):153-63 (abstract only).
Khripin CY et al., "Protein-directed assembly of arbitrary three-dimensional nanoporous silica architectures," *ACS Nano* 2011;5(2):1401-9.
Khripin CY et al., Supporting information for "Protein-directed assembly of arbitrary three-dimensional nanoporous silica architectures," *ACS Nano* 2011;5(2):1401-9, available at http://pubs.acs.org/doi/suppl/10.1021/nn1031774 (last accessed May 1, 2014) (7 pages).
Kirk SE et al., "Application of environmental scanning electron microscopy to determine biological surface structure," *J. Microsc.* Feb. 2009;233(2):205-24.

Kresge CT et al., "Ordered mesoporous molecular sieves synthesized by a liquid-crystal template mechanism," *Nature* Oct. 1992;359:710-2.
Kröger N et al., "Polycationic peptides from diatom biosilica that direct silica nanosphere formation," *Science* 1999;286:1129-32.
Kröger N et al., "Self-assembly of highly phosphorylated silaffins and their function in biosilica morphogenesis," *Science* 2002;298:584-6.
Kröger N et al., "Species-specific polyamines from diatoms control silica morphology," *Proc. Nat'l Acad. Sci. USA* 2000;97(26):14133-8.
Kröger N, "Prescribing diatom morphology: Toward genetic engineering of biological nanomaterials," *Curr. Opin. Chem. Biol.* 2007;11:662-9.
Kumar A et al., "Origins of the anomalous stress behavior in charged colloidal suspensions under shear," *Phys. Rev. E* Nov. 2010;82(5 Pt 1):051401 (7 pp.).
Le Douarin NM, "The avian embryo as a model to study the development of the neural crest: A long and still ongoing story," *Mech. Dev.* Sep. 2004;121(9):1089-102.
Lee KJ et al., "Recent advances with anisotropic particles," *Curr. Opin. Colloid Interface Sci.* Jun. 2011;16(3):195-202.
Leong HS et al., "Intravital imaging of embryonic and tumor neovasculature using viral nanoparticles," *Nat. Protoc.* Aug. 2010;5(8):1406-17.
Li D et al., "Morphology-controlled synthesis of silica nanotubes through pH- and sequence-responsive morphological change of bacterial flagellar biotemplates," *J. Mater. Chem.* 2012;22:15702-9.
Lim HWG et al., "Stomatocyte-discocyte-echinocyte sequence of the human red blood cell: evidence for the bilayer-couple hypothesis from membrane mechanics," *Proc. Natl. Acad. Sci. USA* Dec. 2002;99(26):16766-9.
Lipka J et al., "Biodistribution of PEG-modified gold nanoparticles following intratracheal instillation and intravenous injection," *Biomaterials* Sep. 2010;31(25):6574-81.
Liu J et al., "Electrostatically mediated liposome fusion and lipid exchange with a nanoparticle-supported bilayer for control of surface charge, drug containment, and delivery," *J. Am. Chem. Soc.* Jun. 10, 2009;131(22):7567-9.
Liu J et al., "Porous nanoparticle supported lipid bilayers (protocells) as delivery vehicles," *J. Am. Chem. Soc.* Feb. 4, 2009;131(4):1354-5.
Losic D et al., "Diatomaceous lessons in nanotechnology and advanced materials," *Adv. Mater.* 2009;21:2947-58.
Lou YR et al., "Silica bioreplication preserves three-dimensional spheroid structures of human pluripotent stem cells and HepG2 cells," *Sci. Rep.* 2015;5:13635 (9 pp.).
Lu Y et al., "Aerosol-assisted self-assembly of mesostructured spherical nanoparticles," *Nature* Mar. 1999;398:223-6.
Lu Y et al., "Evaporation-induced self-assembly of hybrid bridged silsesquioxane film and particulate mesophases with integral organic functionality," *J. Am. Chem. Soc.* 2000;122(22):5258-61.
Mann S et al., "Synthesis of inorganic materials with complex form," *Nature* Jul. 1996;382:313-8.
McIntosh R et al., "New views of cells in 3D: An introduction to electron tomography," *Trends Cell Biol.* Jan. 2005;15(1):43-51.
Merkel TJ et al., "Scalable, shape-specific, top-down fabrication methods for the synthesis of engineered colloidal particles," *Langmuir* Aug. 20010;26(16):13086-96.
Merkel TJ et al., "Using mechanobiological mimicry of red blood cells to extend circulation times of hydrogel microparticles," *Proc. Nat'l Acad. Sci. USA* 2011;108(2):586-91.
Meunier CF et al., "Encapsulation of cells within silica matrixes: Towards a new advance in the conception of living hybrid materials," *J. Colloid Interface Sci.* 2010;342:211-24.
Meyer KC et al., "Mechanically encoded cellular shapes for synthesis of anisotropic mesoporous particles," *J. Am. Chem. Soc.* 2014;136:13138-41.
Meyer KC et al., Supporting information for "Mechanically encoded cellular shapes for synthesis of anisotropic mesoporous particles," *J. Am. Chem. Soc.* 2014;136:13138-41 (10 pp.).

(56) References Cited

OTHER PUBLICATIONS

Miyako E et al., "Self-assembled carbon nanotube honeycomb networks using a butterfly wing template as a multifunctional nanobiohybrid," *ACS Nano* 2013;7:8736-42.

Moghaddam S et al., "An inorganic-organic proton exchange membrane for fuel cells with a controlled nanoscale pore structure," *Nat. Nanotechnol.* Mar. 2010;5(3):230-6.

Mohandas N et al., "Red cell membrane: past, present, and future," *Blood* Nov. 2008;112(10):3939-48.

Niu L et al., "Infiltration of silica inside fibrillar collagen," *Angew. Chem. Int. Ed. Engl.* 2011;50:11688-91.

Oberdörster G et al., "Toxicology of nanoparticles: A historical perspective," *Nanotoxicology* 2007;1(1):2-25.

Ohta K et al., "Beam deceleration for block-face scanning electron microscopy of embedded biological tissue," *Micron* Apr. 2012;43(5):612-20.

Pal S, "Mechanical properties of biological materials," in Design of Artificial Human Joints & Organs, Springer Science + Business Media, New York, NY, 2014, pp. 23-40.

Palmer AF et al., "Blood substitutes," *Annu. Rev. Biomed. Eng.* 2014;16:77-101.

Paris O et al., "Biomimetics and biotemplating of natural materials," *MRS Bull.* 2010;35:219-25.

Patwardhan SV et al., "On the role(s) of additives in bioinspired silicification," *Chem. Commun.* 2005;9:1113-21.

Perutz MF, "Submicroscopic structure of the red cell," *Nature* Feb. 1948;161(4084): 204-5.

Pluk H et al., "Advantages of indium-tin oxide-coated glass slides in correlative scanning electron microscopy applications of uncoated cultured cells," *J. Microsc.* Mar. 2009;233(3):353-63.

Pouget E et al., "Hierarchical architectures by synergy between dynamical template self-assembly and biomineralization," *Nat. Mater.* 2007;6:434-9.

Rempe S et al., "Biomimetic membranes for water purification," *Sandia Report No. SAND2011-2061P*, 2011 (28 pp.).

Roh KH et al., "Biphasic Janus particles with nanoscale anisotropy," *Nat. Mater.* Oct. 2005;4(10):759-63.

Rong J et al., "Tobacco mosaic virus templated synthesis of one dimensional inorganic-polymer hybrid fibres," *J. Mater. Chem.* 2009;19:2841-5.

Sandhage KH, "Materials 'alchemy': Shape-preserving chemical transformation of micro-to-macroscopic 3-D structures," *JOM (Journal of the Minerals, Metals & Materials Society (TMS))* Jun. 2010;62(6):32-43.

Scheffel A et al., "Nanopatterned protein microrings from a diatom that direct silica morphogenesis," *Proc. Nat'l Acad. Sci. USA* 2011;108:3175-80.

Schnepp Z et al., "Biotemplating of metal carbide microstructures: the magnetic leaf," *Angew. Chem. Int. Ed. Engl.* Sep. 3, 2010;49(37):6564-6.

Schreier S et al., "Surface active drugs: self-association and interaction with membranes and surfactants. Physicochemical and biological aspects," *Biochim. Biophys. Acta* Nov. 2000;1508(1-2):210-34.

Severs NJ, "Freeze-fracture electron microscopy," *Nat. Protoc.* 2007;2(3):547-76 (abstract only).

She S et al., "Fabrication of red-blood-cell-like polyelectrolyte microcapsules and their deformation and recovery behavior through a microcapillary," *Adv. Mater.* 2013;25:5814-8.

Sheetz MP et al., "Biological membranes as bilayer couples: A molecular mechanism of drug-erythrocyte interactions," *Proc. Nat'l Acad. Sci. USA* Nov. 1974;71(11):4457-61.

Shenton W et al., "Inorganic-organic nanotube composites from templated mineralization of tobacco mosaic virus," *Adv. Mater.* 1999;11(3):253-6.

Shopsowitz KE et al., "Free-standing mesoporous silica films with tunable chiral nematic structures," *Nature* 2010;468:422-5.

Shum HC et al., "Droplet microfluidics for fabrication of non-spherical particles," *Macromol. Rapid Commun.* Jan. 2010;31(12):108-18.

Sing KSW et al., "Reporting physisorption date for gas/solid systems with special reference to the determination of surface area and porosity (Recommendations 1984)," *J. Pure Appl. Chem.* 1985;57(4):603-19.

Stein A et al., "Morphological control in colloidal crystal templating of inverse opals, hierarchical structures, and shaped particles," *Chem. Mater.* 2008;20:649-66.

Stepankova V et al., "Strategies for stabilization of enzymes in organic solvents," *ACS Catal.* 2013;3(12):2823-36.

Sun T et al., "Synthesis of microporous transition-metal-oxide molecular sieves by a supramolecular templating mechanism," *Nature* 1997;389:704-6.

Taney PT et al, "A neutral templating route to mesoporous molecular sieves," *Science* 1995;267:865-7.

Tao Z et al., "Microparticle, nanoparticle, and stem cell-based oxygen carriers as advanced blood substitutes," *Trends Biotechnol.* 2014;32(9):466-73.

Tesson B et al., "Extensive and intimate association of the cytoskeleton with forming silica in diatoms: Control over patterning on the meso- and micro-scale," *PloS One* 2010;5:e14300 (13 pages).

Torquato S et al., "Jammed hard-particle packings: From Kepler to Bernal and beyond," *Rev. Mod. Phys.* Sep. 2010;82(3):2633-72.

Townley HE et al., "Modification of the physical and optical properties of the frustule of the diatom Coscinodiscus wailesii by nickel sulfate," *Nanotechnology* 2007;18:295101-6.

Townson JL et al., "Synthetic fossilization of soft biological tissues and their shape-preserving transformation into silica or electron-conductive replicas," *Nat. Commun.* Dec. 2014;5:5665 (8 pp.).

Townson JL et al., Supporting information for "Synthetic fossilization of soft biological tissues and their shape-preserving transformation into silica or electron-conductive replicas," *Nat. Commun.* Dec. 2014;5:5665 (8 pp.).

Ushiki T et al., "Low-voltage backscattered electron imaging of non-coated biological samples in a low-vacuum environment using a variable-pressure scanning electron microscope with a YAG-detector," *J. Electron Microsc. (Tokyo)* 1998;47(4):351-4 (abstract only).

Van Bommel KJC et al., "Organic templates for the generation of inorganic materials," *Angew. Chem. Int. Ed. Engl.* 2003;42(9):980-99.

Van Opdenbosch D et al., "Silica replication of the hierarchical structure of wood with nanometer precision," *J. Mater. Res.* May 2011;26(10):1193-202.

Walker DA et al., "Geometric curvature controls the chemical patchiness and self-assembly of nanoparticles," *Nat. Nanotechnol.* ; Sep. 2013;8(9):676-81.

Walther A et al., "Janus particles: synthesis, self-assembly, physical properties, and applications," *Chem. Rev.* Jul. 10, 2013;113(7):5194-261.

Wang Y et al., "Nanoporous polyelectrolyte spheres prepared by sequentially coating sacrificial mesoporous silica spheres," *Angew. Chem.* 2005;117:2948-52.

Wang Y et al., "Template synthesis of stimuli-responsive nanoporous polymer-based spheres via sequential assembly," *Chem. Mater.* 2006;18:4089-100.

Warnock JN et al., "Bioreactor systems for the production of biopharmaceuticals from animal cells," *Biotechnol. Appl. Biochem.* 2006;45:1-12.

Wei Y et al., "A novel method for enzyme immobilization: direct encapsulation of acid phosphatase in nanoporous silica host materials," *J. Nanosci. Nanotechnol.* Mar. 2001;1(1):83-93.

Wei Y et al., "Preparation and physisorption characterization of D-glucose-templated mesoporous silica sol-gel materials," *Chem. Mater.* 1999;11:2023-9.

Wilson BS, et al., "Calcium-dependent clustering of inositol 1,4,5-trisphosphate receptors," *Mol. Biol. Cell* Jun. 1998;9:1465-78.

Wong P, "A basis of echinocytosis and stomatocytosis in the disc-sphere transformations of the erythrocyte," *J. Theor. Biol.* Feb. 7, 1999;196(3):343-61.

Xing Z et al., "Scale-up analysis for a CHO cell culture process in large-scale bioreactors," *Biotechnol. Bioeng.* Jul. 2009;103(4):733-46.

(56) References Cited

OTHER PUBLICATIONS

Xu J et al., "Future of the particle replication in nonwetting templates (PRINT) technology," *Angew. Chem. Int. Ed.* 2013;52:6580-9.

Yan J et al., "Linking synchronization to self-assembly using magnetic Janus colloids," *Nature* Nov. 2012;491(7425):578-81.

Yin Y et al., "Template-assisted self-assembly: a practical route to complex aggregates of monodispersed colloids with well-defined sizes, shapes, and structures," *J. Am. Chem. Soc.* Sep. 2001;123(36):8718-29.

Zeming KK et al., "Rotational separation of non-spherical bioparticles using I-shaped pillar arrays in a microfluidic device," *Nat. Commun.* 2013;4:1625 (8 pp.).

Zhang L et al., "Nanoparticles in medicine: Therapeutic applications and developments," *Clin. Pharmacol. Ther.* May 2008;83(5):761-9.

Zhao D et al., "Triblock copolymer syntheses of mesoporous silica with periodic 50 to 300 angstrom pores," *Science* 1998;279(5350):548-52.

Zimmerman AB et al., "Titania and silica materials derived from chemically dehydrated porous botanical templates," *Chem. Mater.* 2012;24(22):4301-10.

Salmaso S et al., "Stealth properties to improve therapeutic efficacy of drug nanocarriers," *J. Drug Delivery* 2013;374252 (19 pp.).

Yang SH et al., "Formation of thiol-functionalized silica films by layer-by-layer self-assembly and biomimetic silicification," *Macromolec. Res.* 2011;19:511-4.

Yang SH et al., "Biomimetic encapsulation of individual cells with silica," *Angew. Chem. Int. Ed.* 2009;48:9160-3.

Yang SH et al., Supporting Information for "Biomimetic encapsulation of individual cells with silica," *Angew. Chem. Int. Ed.* 2009;48:9160-3 (4 pp.).

\* cited by examiner

SHAPE-PRESERVING POLYMERIC REPLICATION OF BIOLOGICAL MATTER

CROSS-REFERENCE TO RELATED APPLICATION

This application is a divisional of prior application Ser. No. 15/282,511, filed Sep. 30, 2016, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to a method of forming silica nanolayers on or within a biological sample, thereby capturing structural details that are present in the sample. The resultant silica composite or silica replica, in turn, can be employed as a template for a construct having those structural details captured in a polymer. Also provided herein are synthetic constructs including such polymeric replica, which can have any useful feature (e.g., oxygen-binding capacity).

BACKGROUND OF THE INVENTION

Complex structures encountered in biological samples can be difficult to replicate synthetically. Yet, there is a demand for controlled manufacturing of three-dimensional, intricate structures formed from durable materials. In addition, hybrid materials (e.g., including both durable synthetic polymers and stabilized biological proteins) can provide orthogonally beneficial properties. In one non-limiting instance, artificial oxygen carriers can include synthetic particles with biological hemoglobin, which can be used as blood substitutes having non-immunogenic properties controlled by choice of the synthetic starting materials and having enhanced oxygen-carrying capacity provided by hemoglobin proteins. Thus, there is a need for methodologies that provide controlled formation of complex structures that can be templated from biological samples.

SUMMARY OF THE INVENTION

Accordingly, the present invention, in part, provides a method to replicate a biological sample (e.g., biological cells, tissues, and 3D (soft) organic matter) into a synthetic material (e.g., a polymeric material). In one non-limiting example, a red blood cell (RBC) can be used as a template to derive a synthetic polymeric replica with retained shape, tunable stiffness, and/or biological function. In one non-limiting instance, the polymer can be designed to respond to environmental signals (e.g., pH, temperature, analyte concentration, etc.) and/or to possess controlled degradation and/or stealth properties in vivo (e.g., by use of poly(ethylene glycol) groups). The procedure can be applied to any useful biological sample, e.g., single cells, multiple cells, tissues, and organisms, as well as 3D materials that possess similar templatable properties (e.g., a 3D printed protein structure). In some instances, the polymer materials (e.g., a polymeric replica or a polymerized replica) can retain properties of the biological template.

The present invention also relates to synthetic constructs, e.g., formed by employing a silica composite as a template. In one non-limiting instance, the synthetic construct includes a polymeric replica (e.g., in which the construct is then used to develop universal carriers, such as artificial blood, engineered tissues, and other functional materials derived from biological forms).

The processes herein can be employed to provide any useful construct (e.g., composite or replica). For instance, silica composites (e.g., composed of silica and the underlying organic matter of the specimen) can be transformed into a silica replica (e.g., composed primarily of silica), a polymerized composite (e.g., composed of a polymeric material, the underlying organic matter of the specimen, and optionally including silica), or a polymeric replica (e.g., composed primarily of a polymeric material).

Accordingly, in a first aspect, the present invention features a method including: forming a silica composite; exposing the silica composite to one or more polymeric precursors; and polymerizing the one or more polymeric precursors (e.g., thereby forming a polymerized construct). The silica composite can be formed in any useful manner, e.g., by forming one or more silica nanolayers on and/or within biological sample including one or more cells. In some embodiments, the one or more silica nanolayers conform to a biological structure on and/or within the biological sample. In one non-limiting embodiment, the silica composite includes silica in combination with other non-silica material (e.g., biological material and/or biological components).

In some embodiments, the one or more polymeric precursors conform to at least one of the one or more silica nanolayers. In other embodiments, the one or more polymeric precursors (e.g., any described herein) form one or more shape-preserved layers that conform to a biological structure on and/or within the biological sample. In one non-limiting embodiment, the polymerized replica includes polymeric material in combination with other non-polymeric material (e.g., silica, biological material, and/or biological components).

In some embodiments, the method includes (e.g., after the polymerizing step): removing the one or more silica nanolayers, or portions thereof, thereby forming a polymeric replica. In one non-limiting embodiment, the polymeric replica includes substantially polymeric material (e.g., lacks silica, biological material, and/or biological components).

In some embodiments, the method includes (e.g., after the forming step and/or the polymerizing step): digesting one or more biological components present in the biological sample (e.g., thereby forming a silica replica). In one non-limiting embodiment, the silica replica includes substantially silica material (e.g., lacks biological material and/or biological components). Digestion can be performed in any useful manner, e.g., by employing an acid, a detergent, and/or an organic solvent.

In some embodiments, the method (e.g., the exposing step) includes forming a multilayer including a plurality of polymeric precursors having a layer-by-layer assembly. In other embodiments, the plurality of polymeric precursors includes polyelectrolyte pairs including alternating charge within the layer-by-layer assembly.

In some embodiments, the method (e.g., the forming step) includes the formation of one or more silica nanolayers on one or more internal surfaces or external surfaces, or a portion thereof, present on or within the biological sample. In other embodiments, the forming step includes immersing the biological sample in an acidic isotonic solution. In further embodiments, the solution (e.g., having a pH of from about 2 to about 4) includes silicic acid capable of forming the one or more silica nanolayers. In yet other embodiments, the concentration of silicic acid results in a self-limiting reaction between the silicic acid and an internal surface or an external surface present on or within the biological sample.

In some embodiments, the method (e.g., before the forming step) includes: treating the biological sample with one or more fixation agents and/or chemical or biological agents.

In a second aspect, the present invention features a synthetic construct including: a polymeric replica of a biological sample; and an oxygen carrier loaded within the polymeric replica (e.g., within an empty space defined by an internal structure of the biological sample prior to digestion). In some embodiments, the polymeric replica includes a shape-preserved layer including a polymeric precursor or a polymer (e.g., a polymer formed from a polymeric precursor, such as any described herein). In some embodiments, the layer is a multilayer including a plurality of polymeric precursors having a layer-by-layer assembly. In one non-limiting embodiment, the polymeric replica includes substantially polymeric material (e.g., lacks silica, biological material, and/or biological components). In further embodiments, the construct includes one or more endogenous or exogenous oxygen-binding molecules loaded within the polymeric replica.

In some embodiments, the construct further includes a lipid layer coating surrounding a periphery of the construct (e.g., a lipid monolayer, a lipid bilayer, and/or a lipid multilayer, optionally including any other useful component, such as a sterol (e.g., cholesterol), a glycoprotein (e.g., CD47), or a pegylated lipid).

In some embodiments, the construct further includes a particle (e.g., a nanoparticle) or a binding group (e.g., a click-chemistry group) disposed within the construct or on a surface of the construct.

In some embodiments, the oxygen carrier includes a perfluorinated group or an emulsion thereof (e.g., any described herein). In other embodiments, at least one of the one or more endogenous or exogenous oxygen-binding molecules includes hemoglobin, porphyrin, heme protein, hemerythrin, hemocyanin, methemoglobin, or a modified form, a cross-linked form, a polymerized form, a conjugated form, and/or a recombinant form thereof.

In some embodiments, the construct further includes a stabilizer, an antibiotic, a vitamin, a nutrient, a volume expander, and/or a salt (e.g., disposed on a surface of the construct and/or disposed within a solution including the construct).

In any embodiment herein, the biological sample includes an organism, an organ, a tissue biopsy, a tissue section, a cell (e.g., a red blood cell, a neuron, and/or a glial cell), a multicellular sample, a soft tissue sample, a printed protein structure (e.g., a protein hydrogel, such as an albumin hydrogel, avidin hydrogel, lysozyme hydrogel, etc.), a population of cells, a sample from an animal source, a sample from a mammalian source, or a protein (e.g., a functional protein, hemoglobin, etc.).

In any embodiment herein, the one or more polymeric precursors includes $L^1$-$R^m$-$L^2$, in which $R^m$ is any useful chemical group (e.g., a monomer) and each of $L^1$ and $L^2$ is, independently, a reactive group (e.g., a functional group that is one of a cross-linker group, a binding group, or a click-chemistry group, such as any described herein). In other embodiments, each of $L^1$ and $L^2$ is chosen to be one of a reaction pair (e.g., a cross-linker reaction pair, a binding reaction pair, or a click-chemistry reaction pair, such as any described herein).

In any embodiment herein, the one or more polymeric precursors or the polymer includes a poly(ethylene glycol) group (e.g., a multivalent poly(ethylene glycol) precursor having a reactive functional group, such as an amino group, an ester group, etc.), an amino acid (e.g., a poly(amino acid) precursor, such as poly(lysine)), a glycerol group (e.g., a poly(glycerol) precursor), a vinyl group (e.g., a poly(vinyl) precursor or a poly(vinyl alcohol) precursor), and/or an acrylate group (e.g., poly(acrylic acid) precursor or poly (methacrylic acid) precursor)). In further embodiments, the one or more polymeric precursors, after polymerization, is optically transparent.

Additional details follow.

Definitions

As used herein, the term "about" means+/−10% of any recited value. As used herein, this term modifies any recited value, range of values, or endpoints of one or more ranges.

By "cell" is meant a biological unit including, at least, a cell membrane and one or more biomolecules (e.g., proteins, peptides, nucleic acids, and/or polysaccharides). Exemplary cells include a red blood cell, a eukaryotic cell, or a prokaryotic cell. Additional cells are described herein.

By "composite" is meant a structure including a sample, or a portion thereof (e.g., organic matter from the sample, such as one or more biocomponents and/or biomolecules), and one or more inorganic nanolayers (e.g., silica nanolayers). Exemplary samples include biological samples, such as a cell, a tissue sample, a population of cells, an organ, an embryo, etc. In one instance, the composite is a polymerized silica composite including one or more inorganic silica nanolayers, a polymeric material, and organic matter from the sample. In another instance, the composite is a polymerized composite including a polymeric material and organic matter from the sample.

By "replica" is meant a structure derived from a composite, as defined herein, but lacking the organic matter from the sample in its native form. In one instance, the replica is a silica replica including one or more inorganic silica nanolayers. In another instance, the replica is a polymerized silica replica including one or more inorganic silica nanolayers and a polymeric material. In yet another instance, the replica is a polymeric replica including a polymeric material templated from the sample but lacking a silica nanolayer. Other replicas and composites are described herein.

By "silicic acid" is meant a family of chemical compounds containing the element silicon attached to oxide and/or hydroxyl groups that are capable of condensing and forming oligomeric and/or polymeric silicon dioxide or silica coatings pursuant to the present invention. In one instance, silicic acid is a chemical compound having the structure $Si(OR)_4$, wherein each R is, independently, H or an optionally substituted alkyl, as defined herein (e.g., an optionally substituted $C_{1-6}$ alkyl). In another instance, a silicic acid is selected from the group of orthosilicic acid (generally referred to as silicic acid), metasilicic acid, disilic acid, and pyrosilicic acid, among others. In yet another instance, a silicic acid (including a silicic acid derivative) includes tetramethoxysilane (TMOS), tetraethoxysilane (TEOS), as well as mixtures thereof.

By "micro" is meant having at least one dimension that is less than 1 mm. For instance, a microstructure (e.g., any structure described herein) can have a length, width, height, cross-sectional dimension, circumference, radius (e.g., external or internal radius), or diameter that is less than 1 mm.

By "nano" is meant having at least one dimension that is less than 1 μm. For instance, a nanostructure (e.g., any structure described herein) can have a length, width, height, cross-sectional dimension, circumference, radius (e.g., external or internal radius), or diameter that is less than 1 μm. In some embodiments, a nanolayer is a layer having a thickness (e.g., measured in a dimension that is orthogonal to an external or internal surface) that is of from about 0.01 nm to about 1,000 nm (e.g., of from about 0.01 nm to about 100 nm, such as of from about 0.01 nm to 5 nm, 0.01 nm to 10 nm, 0.01 nm to 20 nm, 0.01 nm to 50 nm, 0.1 nm to 5 nm, 0.1 nm to 10 nm, 0.1 nm to 20 nm, 0.1 nm to 50 nm, 0.1 nm to 100 nm, 1 nm to 5 nm, 1 nm to 10 nm, 1 nm to 20 nm, 1 nm to 50 nm, 1 nm to 100 nm, 2 nm to 5 nm, 2 nm to 10 nm, 2 nm to 20 nm, 2 nm to 50 nm, 2 nm to 100 nm, 4 nm to 5 nm, 4 nm to 10 nm, 4 nm to 20 nm, 4 nm to 50 nm, 4 nm to 100 nm, 10 nm to 20 nm, 10 nm to 50 nm, or 10 nm to 100 nm).

As used herein, the terms "top," "bottom," "upper," "lower," "above," and "below" are used to provide a relative relationship between structures. The use of these terms does not indicate or require that a particular structure must be located at a particular location in the apparatus.

The term "acyl," or "alkanoyl," as used interchangeably herein, represent an alkyl group, as defined herein, or hydrogen attached to the parent molecular group through a carbonyl group, as defined herein. This group is exemplified by formyl, acetyl, propionyl, butanoyl, and the like. The alkanoyl group can be substituted or unsubstituted. For example, the alkanoyl group can be substituted with one or more substitution groups, as described herein for alkyl. In some embodiments, the unsubstituted acyl group is a $C_{2-7}$ acyl or alkanoyl group.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkcycloalkyl" is meant a cycloalkyl group, as defined herein, attached to the parent molecular group through an alkylene group, as defined herein. Exemplary unsubstituted alkcycloalkyl groups are of from 4 to 14 carbons ($C_{4-14}$ alkaryl), as well as those having an alkylene group with 1 to 6 carbons and a cycloalkyl group with 3 to 8 carbons (i.e., $C_{1-6}$ alk-$C_{3-8}$ aryl).

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{2-8}$ alkenyl; (2) $C_{2-8}$ alkynyl; (3) $C_{1-6}$ alkoxy (e.g., —OR$^Y$); (4) $C_{1-6}$ alkylsulfinyl (e.g., —S(O)R$^Y$); (5) $C_{1-6}$ alkylsulfonyl (e.g., —SO$_2$R$^Y$); (6) amino; (7) aryl (e.g., $C_{4-18}$ aryl); (8) arylalkoxy (e.g., —OR$^Z$Ar$^Z$); (9) aryloyl (e.g., —C(O)Ar$^Z$); (10) azido (—N$_3$); (11) carboxyaldehyde (—C(O)H); (12) carboxyl (—C(O)OH); (13) $C_{3-8}$ cycloalkyl; (14) halo; (15) heterocyclyl (e.g., $C_{1-18}$ heterocyclyl including one or more heteroatoms, such as N, O, S, and P); (16) heterocyclyloxy (e.g., —OHet$^Z$); (17) heterocyclyloyl (e.g., —C(O)Het$^Z$); (18) hydroxyl; (19) N-protected amino; (20) nitro (—NO$_2$); (21) oxo (=O); (22) $C_{3-8}$ spirocyclyl; (23) $C_{1-6}$ thioalkoxy (e.g., —SR); (24) thiol (—SH); (25) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (26) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (27) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (28) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (29) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, where in one embodiment no two groups are bound to the nitrogen atom through a carbonyl group or a sulfonyl group (e.g., where R$^Y$ is alkyl (e.g., $C_{1-6}$ alkyl), R$^Z$ is alkylene (e.g., $C_{1-6}$ alkylene), Ar$^Z$ is aryl (e.g., $C_{4-18}$ aryl), and Het$^Z$ is heterocyclyl (e.g., $C_{1-18}$ heterocyclyl including one or more heteroatoms, such as N, O, S, and P), as defined herein). The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkenyl" is meant an optionally substituted $C_{2-24}$ alkyl group having one or more double bonds. The alkenyl group can be cyclic (e.g., $C_{3-24}$ cycloalkenyl) or acyclic. The alkenyl group can also be substituted or unsubstituted. For example, the alkenyl group can be substituted with one or more substitution groups, as described herein for alkyl. In some embodiments, the unsubstituted alkenyl group is a $C_{2-6}$, $C_{2-12}$, $C_{2-18}$, or $C_{2-24}$ alkenyl group.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl (e.g., alkoxy that is optionally substituted with one or more substitution groups, such as alkyl, haloalkyl, halo, etc.). Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkoxyalkyl" is meant an alkoxy group, as defined herein, attached to the parent molecular group through an alkylene group, as defined herein. The alkoxyalkyl group can be substituted or unsubstituted. For example, the alkoxyalkyl group can be substituted with one or more substitution groups, as described herein for alkyl. Exemplary unsubstituted alkoxyalkyl groups are of from 2 to 12 carbons ($C_{2-12}$ alkoxyalkyl), as well as those having an alkylene group with 1 to 6 carbons and an alkoxy group with 1 to 6 carbons (i.e., $C_{1-6}$ alkoxy-$C_{1-6}$ alkyl).

By "alkylene" is meant a bivalent form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "alkyleneoxy" is meant an alkylene group, as defined herein, attached to the parent molecular group through an oxygen atom.

By "alkynyl" is meant an optionally substituted $C_{2-24}$ alkyl group having one or more triple bonds. The alkynyl group can be cyclic or acyclic and is exemplified by ethynyl, 1-propynyl, and the like. The alkynyl group can also be substituted or unsubstituted. For example, the alkynyl group can be substituted with one or more substitution groups, as described herein for alkyl. In some embodiments, the unsubstituted alkynyl group is a $C_{2-6}$, $C_{2-12}$, $C_{2-18}$, or $C_{2-24}$ alkynyl group.

By "amido" is meant —$NR^{N1}(C(O)R^{N3})$, where $R^{N1}$ is H or optionally substituted alkyl and $R^{N3}$ is H, optionally substituted alkyl, or haloalkyl.

By "amino" is meant —$NR^{N1}R^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocyclyl group, as defined herein.

By "aminoalkyl" is meant an alkyl group, as defined herein, substituted by one to three amino groups, with the proviso that no more than one amino group may be attached to a single carbon atom of the alkyl group and is exemplified by aminomethyl, diaminopropyl, and the like.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —$C(O)R^Y$ or —$C(O)H$); (2) $C_{1-6}$ alkyl; (3) $C_{1-6}$ alkoxy; (4) $C_{1-6}$ alkoxy-$C_{1-6}$ alkyl (e.g., —$R^Z OR^Y$); (5) $C_{1-6}$ alkylsulfinyl (e.g., —$S(O)R^Y$); (6) $C_{1-6}$ alkylsulfinyl-$C_{1-6}$ alkyl (e.g., —$R^Z S(O)R^Y$); (7) $C_{1-6}$ alkylsulfonyl (e.g., —$SO_2 R^Y$); (8) $C_{1-6}$ alkylsulfonyl-$C_{1-6}$ alkyl (e.g., —$R^Z SO_2 R^Y$); (9) $C_{2-8}$ alkenyl; (10) $C_{2-8}$ alkynyl; (11) aryl (e.g., $C_{4-18}$ aryl); (12) amino; (13) $C_{1-6}$ aminoalkyl (e.g., —$R^Z NR^{N1} R^{N2}$, as defined herein for amino); (14) heteroaryl (e.g., $C_{1-18}$ heteroaryl including one or more heteroatoms, such as N, O, S, and P); (15) $C_{1-6}$ alk-$C_{4-18}$ aryl (e.g., —$R^Z Ar^Z$); (16) aryloyl (e.g., —$C(O)Ar^Z$); (17) azido (—$N_3$); (18) $C_{1-6}$ azidoalkyl (e.g., —$R^Z N_3$); (19) carboxyaldehyde (—$C(O)H$); (20) carboxyaldehyde-$C_{1-6}$ alkyl (e.g., —$R^Z C(O)H$); (21) $C_{3-8}$ cycloalkyl; (22) $C_{1-6}$ alk-$C_{3-8}$ cycloalkyl (e.g., —$R^Z R^{Cy}$); (23) halo; (24) $C_{1-6}$ haloalkyl; (25) heterocyclyl (e.g., $C_{1-18}$ heterocyclyl including one or more heteroatoms, such as N, O, S, and P); (26) heterocyclyloxy (e.g., —$OHet^Z$); (27) heterocyclyloyl (e.g., —$C(O)Het^Z$); (28) hydroxyl; (29) $C_{1-6}$ hydroxyalkyl (e.g., —$R^Z (OH)_{1-3}$); (30) nitro (—$NO_2$); (31) $C_{1-6}$ nitroalkyl (e.g., —$R^Z (NO_2)_{1-3}$); (32) N-protected amino; (33) N-protected amino-$C_{1-6}$ alkyl; (34) oxo (=O); (35) $C_{1-6}$ thioalkoxy (e.g., —$SR^Y$); (36) thio-$C_{1-6}$ alkoxy-$C_{1-6}$ alkyl (e.g., —$R^Z SR^Y$); (37) —$(CH_2)_r CO_2 R^A$, where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_r CONR^B R^C$, where r is an integer of from zero to four and where each $R^B$ and $R^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (39) —$(CH_2)_r SO_2 R^D$, where r is an integer of from zero to four and where $R^D$ is selected from the group consisting of (a) $C_{1-6}$ alkyl, (b) $C_{4-18}$ aryl, and (c) $C_{1-6}$ alk-$C_{4-18}$ aryl; (40) —$(CH_2)_r SO_2 NR^E R^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (41) —$(CH_2)_r NR^G R^H$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, where in one embodiment no two groups are bound to the nitrogen atom through a carbonyl group or a sulfonyl group; (42) thiol (—SH); (43) perfluoroalkyl; (44) perfluoroalkoxy (e.g., —$OR^F$); (45) aryloxy (e.g., —$OAr^Z$); (46) cycloalkoxy (e.g., —$OR^{Cy}$); (47) cycloalkylalkoxy (e.g., —$OR^Z R^{Cy}$); and (48) arylalkoxy (e.g., —$OR^Z Ar^Z$)) (e.g., where $R^Y$ is alkyl (e.g., $C_{1-6}$ alkyl), $R^Z$ is alkylene (e.g., $C_{1-6}$ alkylene), $Ar^Z$ is aryl (e.g., $C_{4-18}$ aryl), $Het^Z$ is heterocyclyl (e.g., $C_{1-18}$ heterocyclyl including one or more heteroatoms, such as N, O, S, and P), $R^{Cy}$ is cycloalkyl (e.g., $C_{3-8}$ cycloalkyl), and $R^E$ is perfluoroalkyl (e.g., $C_{1-6}$ perfluoroalkyl), as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a bivalent form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl.

By "carbonyl" and the suffix "oyl" is meant —C(O)—.

By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl group can also be substituted or unsubstituted. For example, the cycloalkyl group can be substituted with one or more groups including those described herein for alkyl.

By "halo" is meant F, Cl, Br, or I.

By "haloalkyl" is meant an alkyl group, as defined herein, substituted with one or more halo. Exemplary haloalkyl groups include $C_{1-3}$, $C_{1-6}$, $C_{1-12}$, $C_{1-16}$, $C_{1-18}$, $C_{1-20}$, or $C_{1-24}$ haloalkyl groups.

By "heteroalkylene" is meant an alkylene group, as defined herein, containing one, two, three, or four non-carbon heteroatoms (e.g., independently selected from the group consisting of nitrogen, oxygen, phosphorous, sulfur, or halo).

By "heteroalkyleneoxy" is meant a heteroalkylene group, as defined herein, attached to the parent molecular group through an oxygen atom. Exemplary heteroalkyleneoxy groups include a divalent amido group (e.g., —N(R$^{N1}$)C(O)— or —N=C(R$^{N1}$)O—, where R$^{N1}$ is H, optionally substituted alkyl, or optionally substituted haloalkyl).

By "heteroaryl" is meant a subset of heterocyclyl groups, as defined herein, which are aromatic, i.e., they contain 4n+2 pi electrons within the mono- or multicyclic ring system.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, silicon, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like. Exemplary unsubstituted heterocyclyl groups include $C_{1-12}$, $C_{1-14}$, $C_{1-18}$, $C_{1-24}$, $C_{2-12}$, $C_{2-14}$, $C_{2-18}$, $C_{2-24}$, $C_{3-12}$, $C_{3-14}$, $C_{3-18}$, or $C_{3-24}$ heterocyclyl including one or more heteroatoms, such as N, O, S, Si, P, and halo.

By "hydroxyl" is meant —OH.

By "hydroxyalkyl" is meant an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like. Exemplary hydroxyalkyl groups include (hydroxyl)$_{1-3}$-$C_{1-3}$, $C_{1-6}$, $C_{1-12}$, $C_{1-16}$, $C_{1-18}$, $C_{1-20}$, or $C_{1-24}$ hydroxyalkyl groups.

By "perfluoroalkyl" is meant an alkyl group, as defined herein, having each hydrogen atom substituted with a fluorine atom. Exemplary perfluoroalkyl groups include trifluoromethyl, pentafluoroethyl, etc. Exemplary perfluoroalkyl groups include $(CF_2)_{nf}CF_3$ groups, where nf is an integer from 0 to 24.

By "perfluoroalkylene" is meant an alkylene group, as defined herein, having each hydrogen atom substituted with a fluorine atom. Exemplary perfluoroalkylene groups include difluoromethylene, tetrafluoroethylene, etc.

By "perfluoroalkyleneoxy" is meant a perfluoroalkylene group, as defined herein, having an oxy group attached to either end of the perfluoroalkylene group. Exemplary perfluoroalkylene groups include, e.g., —OC$_f$F$_{2f}$— or —C$_f$F$_{2f}$O—, where f is an integer from about 1 to 5, and 2f is an integer that is 2 times f (e.g., difluoromethyleneoxy, tetrafluoroethyleneoxy, etc.).

By "perfluoroalkoxy" is meant an alkoxy group, as defined herein, having each hydrogen atom substituted with a fluorine atom.

By "salt" is meant an ionic form of a compound or structure (e.g., any formulas, compounds, or compositions described herein), which includes a cation or anion compound to form an electrically neutral compound or structure. Salts, including pharmaceutically acceptable salts, are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth. The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "sulfonate" is meant —OSO$_2$—R$^{S1}$, where R$^{S1}$ is an organic moiety (e.g., optionally substituted alkyl, haloalkyl, aryl, or alkaryl).

Other features and advantages of the invention will be apparent from the following description and the claims.

DETAILED DESCRIPTION OF THE INVENTION

The present invention relates to methods of forming silica composites and resultant constructs formed from a polymeric material. Such constructs can include hybrid composites (e.g., including a polymeric material and underlying organic matter) and replicas (e.g., including primarily a polymeric material). In particular, the methods and constructs herein include the use of biological samples, which serve as a structurally-rich template having both internal and external surfaces capable of supporting a silica nanolayer. These surfaces are not disturbed by the silica precursors (e.g., silicic acid and related compounds) but preserved by the nanolayer(s). In some embodiments, the extensive and conformal nature of the deposited nanolayers allow the underlying biological sample to be removed or pyrolyzed without harming the structural details captured by the nanolayers. The nanolayers can also serve as a shape-preserved template, upon which polymeric precursors can be deposited and polymerized to form a durable polymeric material (e.g., a polymeric hydrogel). Additional details on the constructs and methods of the invention follow.

Constructs (Composites and Replicas) and the Silification Process

Figure 1A:
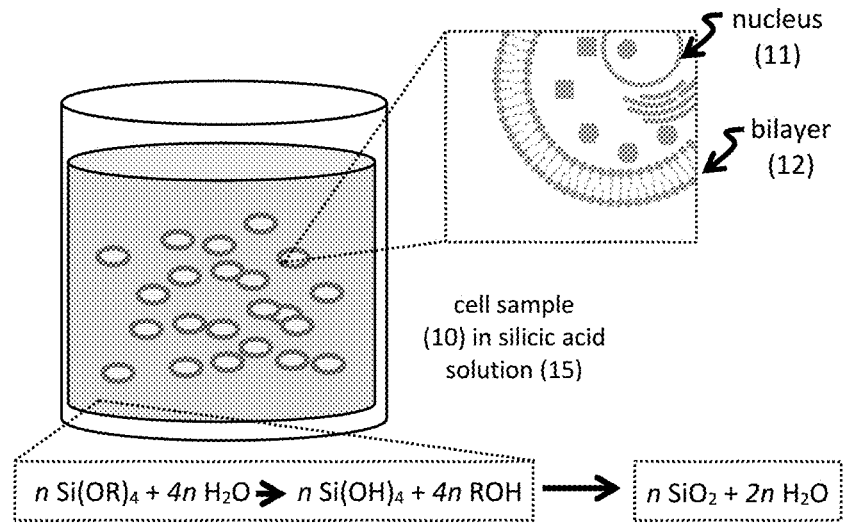
FIG. 1A-1D shows schematics of exemplary silica bioreplication (SBR) processes to provide silica nanolayers and exemplary polymerization processes to provide a polymer-containing composite or replica. Provided are an exemplary SBR process for treating a cell sample 10 in an exemplary silicic acid solution 15 (FIG. 1A); another exemplary SBR process for treating a tissue sample 100 in an exemplary silicic acid solution 150 (FIG. 1B); an exemplary polymerization process to provide a polymerized composite 1040 including internal biocomponents (FIG. 1C); and another exemplary polymerization process to provide a polymeric replica 1140 including internal structures replicated from initial biocomponents (FIG. 1D).
Figure 1B:
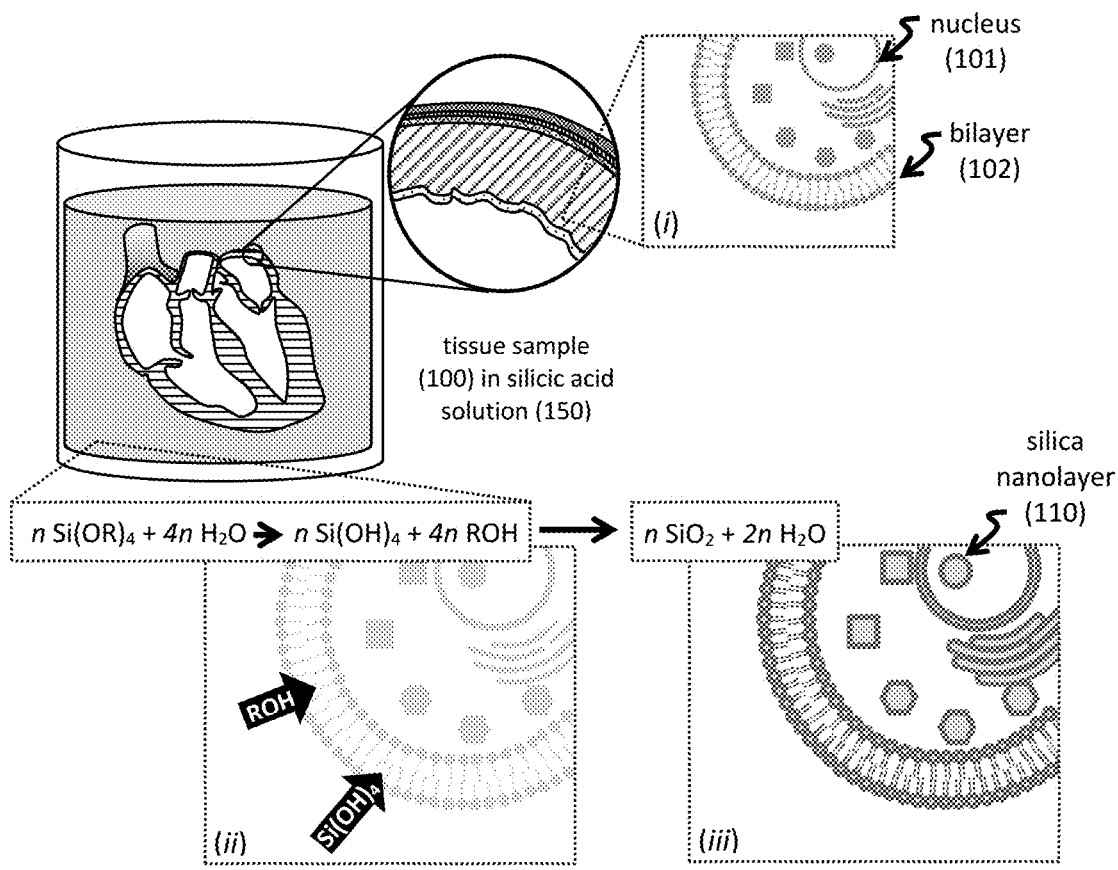

The present invention relates to a construct having one or more nanolayers formed on internal and/or external surfaces of a biological source (e.g., a cell, a tissue, an organ, etc.). In one non-limiting embodiment, the construct is formed by placing a sample 10,100 in a silicic acid solution 15,150 (FIG. 1A-1B). Under particular reaction conditions (e.g., under low pH conditions), a self-limiting condition is provided, in which the silicic acid chemical compound does not form a gel in solution but, instead, allows these silicic acid compounds to deposit on nanostructures and microstructures located on external surface(s), internal surface(s), or portions thereof, of the biological sample (e.g., the nucleus 11 and lipid bilayer 12 of the cell). When silicic acid compounds are in close proximity to cellular and protein surfaces, the resulting atomic-scale and/or nano-scale interactions provide silica nanolayers 110 on the internal and/or external surfaces or portions thereof (FIG. 1B). This process is termed silification or silica bioreplication (SBR) and provides a silica composite.

FIG. 1B provides further detail of an exemplary silification process. As can be seen, the exemplary biological sample is a tissue sample 100 that is immersed in a silicic acid solution 150. The tissue sample 100 includes various cellular components, such as a nucleus 101, a lipid bilayer 102, as well as proteins and other cellular structures (gray geometric figures and curves) shown in the inset labeled (i) of FIG. 1B. The exemplary silicic acid solution 150 includes a silicic acid compound (e.g., $Si(OR)_4$) and a solvent (e.g., $H_2O$), which undergoes a hydrolysis reaction to provide orthosilicic acid $Si(OH)_4$ (also a silicic acid compound) and an alcohol ROH (e.g., R is optionally substituted alkyl, or any described herein). Then, the hydrolyzed silicic acid compound (e.g., $Si(OH)_4$) condenses to form an exemplary silica nanolayer 110 composed of $SiO_2$ (FIG. 1B, inset (iii)).

The chemical reactions of the silicic acid compounds occur on various biological interfaces and at various length scales. For instance, the hydrolysis reaction occurs generally in the bulk volume of the silicic acid solution, but the hydrolysis reaction products (e.g., $Si(OH)_4$ and ROH) enter the cells of the tissue sample (inset (ii) of FIG. 1B). In some embodiments, ROH acts as a cell permeabilizing agent, which facilitates entry of the silicic acid compounds through lipid layers and into various cellular compartments. Once within the cells, the silicic acid compounds interact with various biological interfaces, such as those present on cell structures, proteins, etc. Without wishing to be limited by mechanism, we believe that this interaction relies on hydrogen bonding with biological interfaces and amphoteric catalysis with proximal acidic/basic moieties at these biological interfaces, and that the molecularly crowded conditions present within the cell further promotes silica condensation. Thus, the resultant silica nanolayer 110 is conformal and preserves shapes (e.g., microscale and nanoscale features) of the underlying tissue (inset (iii) of FIG. 1B).

Figure 1C:
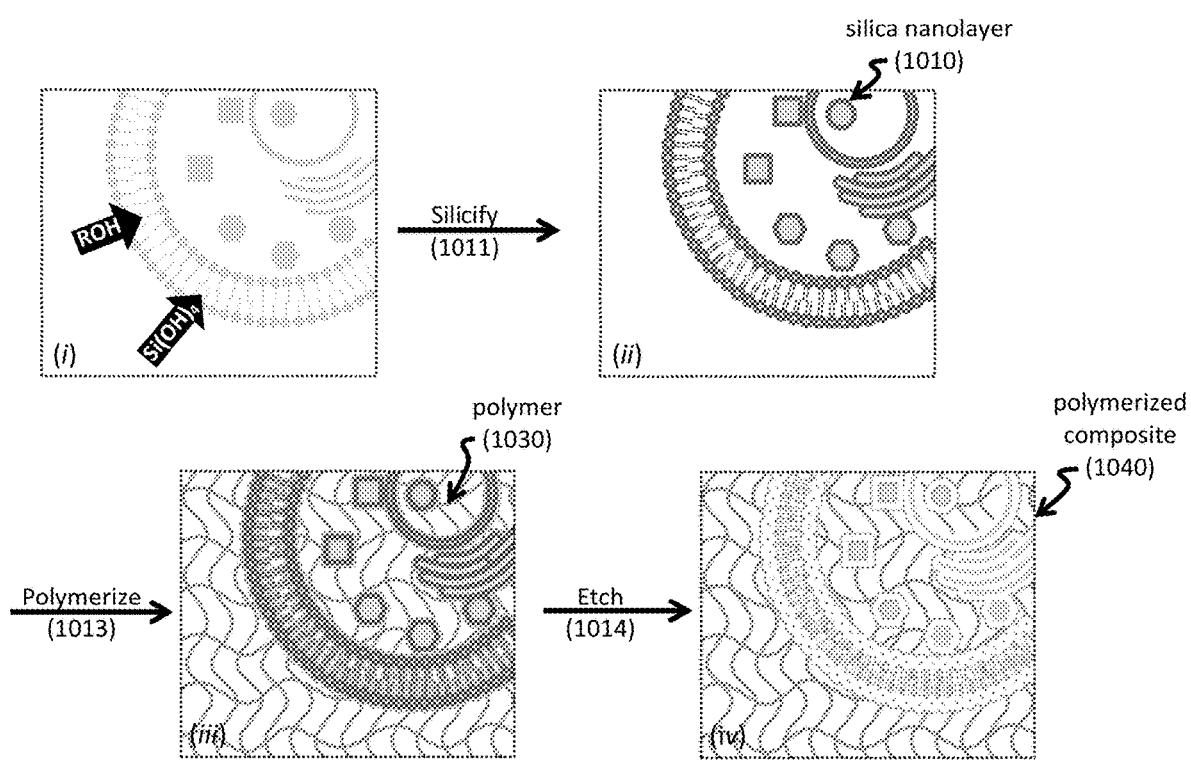

After the SBR process, a silica composite is formed. This silica composite can be used as a template for polymeric precursors, which can then be polymerized to provide a construct having a polymer material. FIG. 1C provides a method including both the SBR process and the polymerization process. As can be seen, a biological sample undergoes the silification process 1011 to provide a silica composite having a silica nanolayer 1010 (FIG. 1C, insets (i) and (ii)). Then, the silica composite is exposed to one or more polymeric precursors, where the one or more polymeric precursors conform to the silica nanolayer(s). Polymerization 1013 of the one or more polymeric precursors provides a polymer 1030. In one non-limiting embodiment, the resultant construct is a polymerized silica composite having a polymer 1030 deposited upon the silica nanolayers 1010 and having underlying organic matter present in the initial biological sample. Etching 1014 of the construct then selectively removes the silica nanolayers, thereby providing a polymerized composite 1040 composed of a polymer and underlying organic matter (e.g., biomolecules, such as proteins, enzymes, and/or lipids) present in the initial biological sample.

Figure 1D:
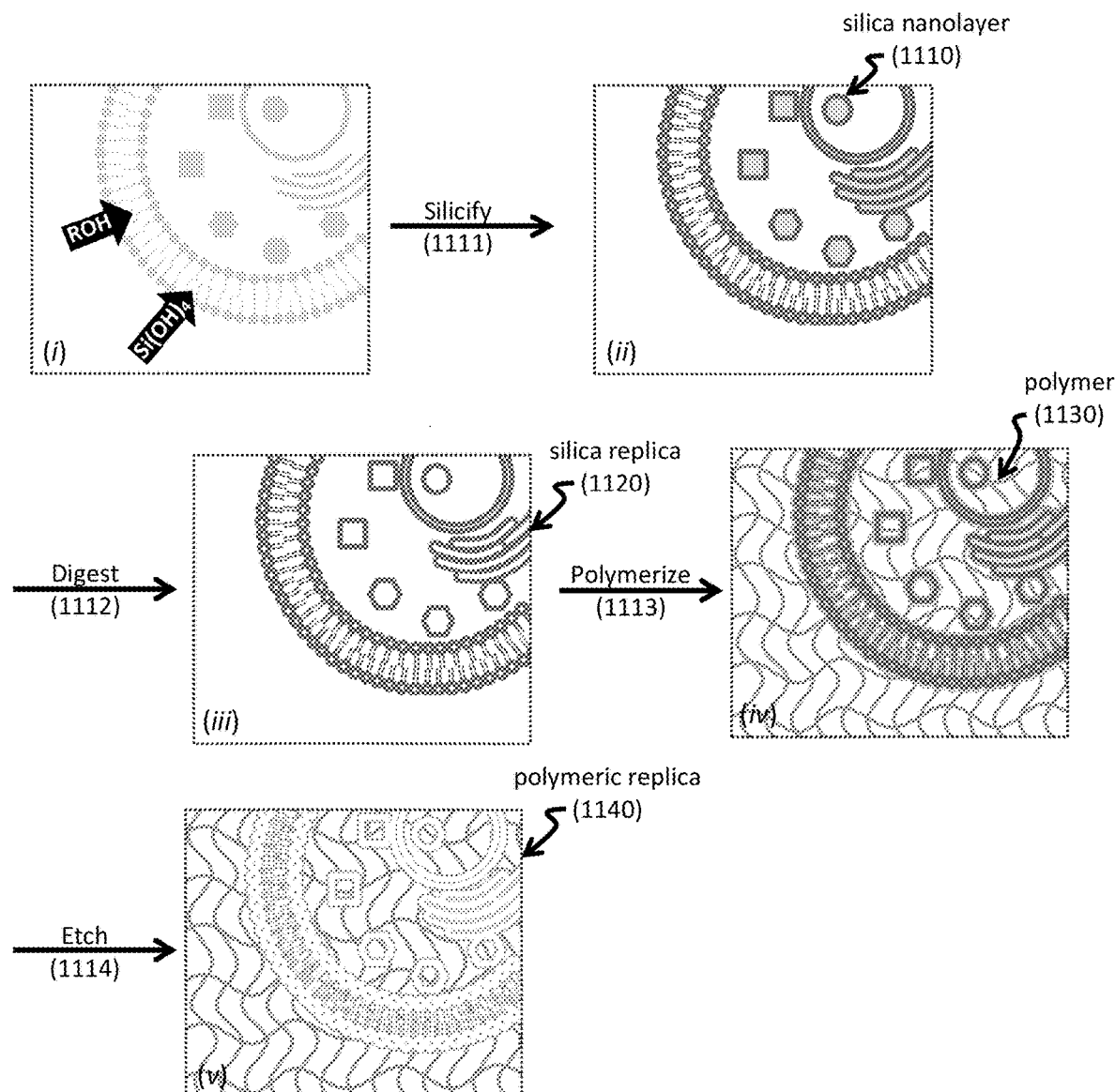

Further step(s) can be implemented to remove the underlying organic matter, or a portion thereof. FIG. 1D provides a method including such as step. As can be seen, a biological sample undergoes the silification process 1111 to provide a silica composite having a silica nanolayer 1110 (FIG. 1D, insets (i) and (ii)). Next, the silica composite is treated to digest 1112 one or more biological components present in the biological sample. In one non-limiting embodiment, the resultant construct is a silica replica 1120 having silica nanolayers 1110 but minimal organic matter contributed from the biological sample. Then, the silica composite is exposed to one or more polymeric precursors, where the one or more polymeric precursors conform to the silica nanolayer(s). Polymerization 1113 of the one or more polymeric precursors provides a polymer 1130. In one non-limiting embodiment, the resultant construct is a polymerized silica replica having a polymer 1130 deposited upon the silica nanolayers 1010. Etching 1114 of the construct then selectively removes the silica nanolayers, thereby providing a polymerized replica 1140 composed of a polymer.

Silica nanolayers can be removed in any useful manner (e.g., use of an etchant, such as hydrofluoric acid (HF), buffered HF, dilute HF solution, nitric acid ($HNO_3$), $HF/HNO_3$ solution, hydrochloric acid (HCl), sodium hydroxide (NaOH), potassium hydroxide (KOH), as well as combinations thereof and/or buffered forms thereof). In some embodiments, etching conditions are optimized to selectively remove silica but retain biological function and/or structure provided by the biological sample. In particular, the silica nanolayers are sufficiently thin such that minimal contact time is required between the etchant and the construct (e.g., of from about seconds to minutes; or less than about 5 minutes).

The biological sample can be treated with one or more agents to alter the shape of the underlying biological sample. For instance, most biological samples are sensitive to external cues, such that exposing the sample to a biological or chemical agent can induce an intercellular or extracellular change that manifests as a structural change. As an example, exposure of a cell to hypertonic conditions (e.g., employing high salt concentrations) can result in osmotic stress, which manifests as shrinking to form a crenated cell. This shrunken, crenated shape can then be silicified, thereby providing a shape-encoded composite that can be further processed into a replica (e.g., any herein).

Figure 2A:
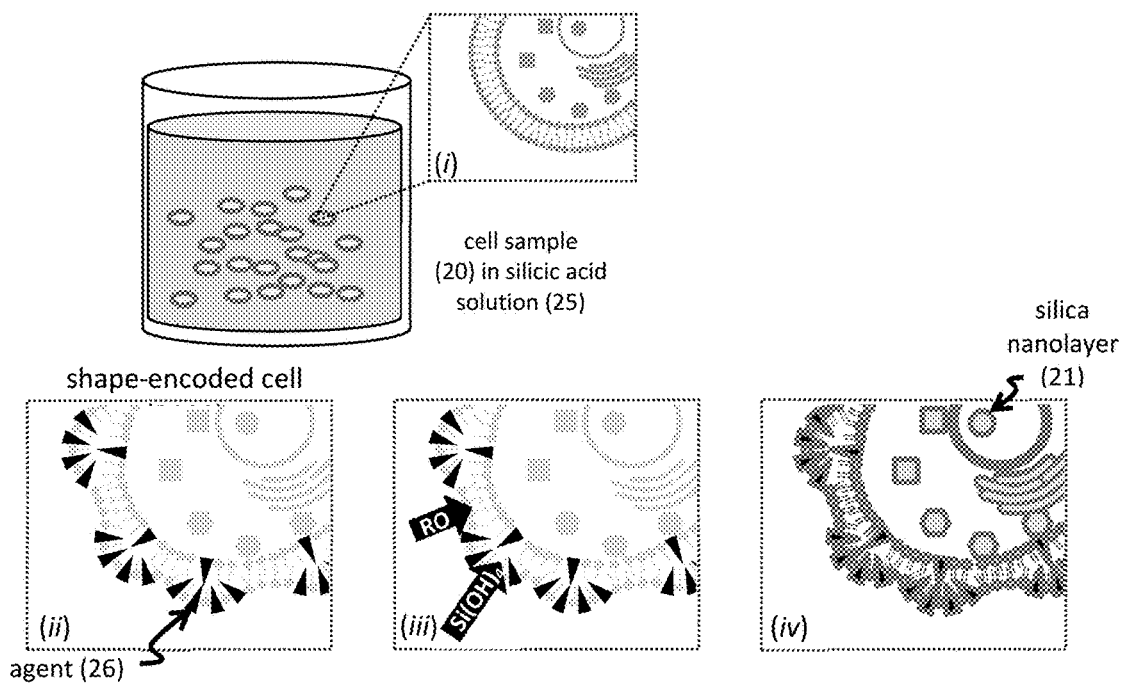
FIG. 2A-2B shows schematics for various processes to form composites and replicas. Provided is an exemplary SBR process to form silica composites from shape-encoded samples 200 (FIG. 2A). Also provided is an exemplary silification and polymerization process to form a polymeric replica 205 composed substantially of polymer and/or a polymerized composite 207 composed of both polymer and carbon-based biocomponents (FIG. 2B).

Any useful sample (e.g., a biological sample, such as those including tissue, cells, etc.) can provide shape-encoded composites and replicas. Of course, the choice of the agent to provide the shape will depend on the type of tissue sample or cell sample, the desired alteration of either internal surfaces or external surfaces, and the desired geometry of the final shape. As seen in FIG. 2A, the exemplary sample is a cell sample 20 that is immersed in a silicic acid solution 25. The sample 20 includes various cellular components, such as a nucleus, a lipid bilayer, as well as proteins and other cellular structures (gray geometric figures and curves) shown in the inset labeled (i) of FIG. 2A.

An agent 26 can be employed to provide a shape-encoded cell. As seen in inset (ii) of FIG. 2A, the agent 26 is selected to alter the lipid bilayer of the cell. The agent can be added either prior to or concurrent with immersing the sample in the silicic acid solution. In addition, one or more agents can be employed together in the same step or in different, subsequent steps. Next, the components of the silicic acid solution (e.g., the silicic acid compound and/or the alcohol) react with the various biological interfaces presented on and within the sample. For instance, silicic acid compound $Si(OH)_4$ and alcohol ROH react with various interfaces (FIG. 2A, inset (iii)), thereby providing a silica composite having one or more silica nanolayers 21 (FIG. 2A, inset (iv)).

The silica nanolayer can have any useful dimension and composition. For instance, the silica nanolayer can be composed of predominantly $SiO_2$. In another instance, the silica nanolayer has a thickness (e.g., along an axis orthogonal to a surface, such as a plane along the external surface of the tissue) of from about 0.1 nm to about 500 nm (e.g., from 1 nm to 500 nm, 1 nm to 250 nm, 1 nm to 100 nm, 1 nm to 50 nm, 1 nm to 25 nm, 1 nm to 10 nm, from 2 nm to 500 nm, 2 nm to 250 nm, 2 nm to 100 nm, 2 nm to 50 nm, 2 nm to 25 nm, 2 nm to 10 nm, from 5 nm to 500 nm, 5 nm to 250 nm, 5 nm to 100 nm, 5 nm to 50 nm, 5 nm to 25 nm, 5 nm to 10 nm, from 10 nm to 500 nm, 10 nm to 250 nm, 10 nm to 100 nm, 10 nm to 50 nm, and 10 nm to 25 nm). In some instances, the nanolayer can be formed from another material, such as a metal, a ceramic, a semiconductor, etc., of any useful thickness (e.g., of from about 0.1 nm to about 500 nm, including any other range described herein).

The construct can have any other useful features. For instance, the construct can be mesoporous (i.e., having pores of a diameter of from about 1.5 nm to about 50 nm). In another instance, the construct is not spherical (i.e., non-spherical). In other instances, the construct possesses stabilized enzymatic activity or stabilized protein structures, in which proteins or enzymes from the biological sample are retained in the construct.

In one instance, the construct is not a monolith. There are at least two critical, structural differences between a silica composite and a silica gel monolith. First, a silica composite includes silica layers deposited within the tissue, whereas a silica monolith includes silica components surrounding only the external surface of the tissue. Second, the silica composite includes nanolayers of silica, whereas the silica monolith includes a gel of silica. Due to these structural and compositional differences, a silica composite captures detailed nanoscopic and microscopic cellular and protein structures of the underlying biological tissue, whereas the silica gel monolith possesses no such details. Thus, the constructs of the present invention are distinct from monoliths or encapsulated structures, in which a tissue is embedded or encapsulated in a silica gel.

In particular, such a monolith and/or an encapsulated structure is a shaped, fabricated, intractable article with a homogeneous microstructure which does not exhibit any structural components distinguishable by optical microscopy, as defined, e.g., in the International Union of Pure and Applied Chemistry (IUPAC) Compendium of Chemical Terminology, 2nd ed. (the "Gold Book") and in Aleman J et al., "Definitions of terms relating to the structure and processing of sols, gels, networks, and inorganic-organic hybrid materials (IUPAC Recommendations 2007)," *Pure Appl. Chem.* 2007; 79(10):1801-29, each of which is incorporated herein by reference in its entirety). Thus, in some embodiments, the construct of the invention is neither a monolith nor an encapsulated gel structure.

Types of Constructs

Figure 2B:
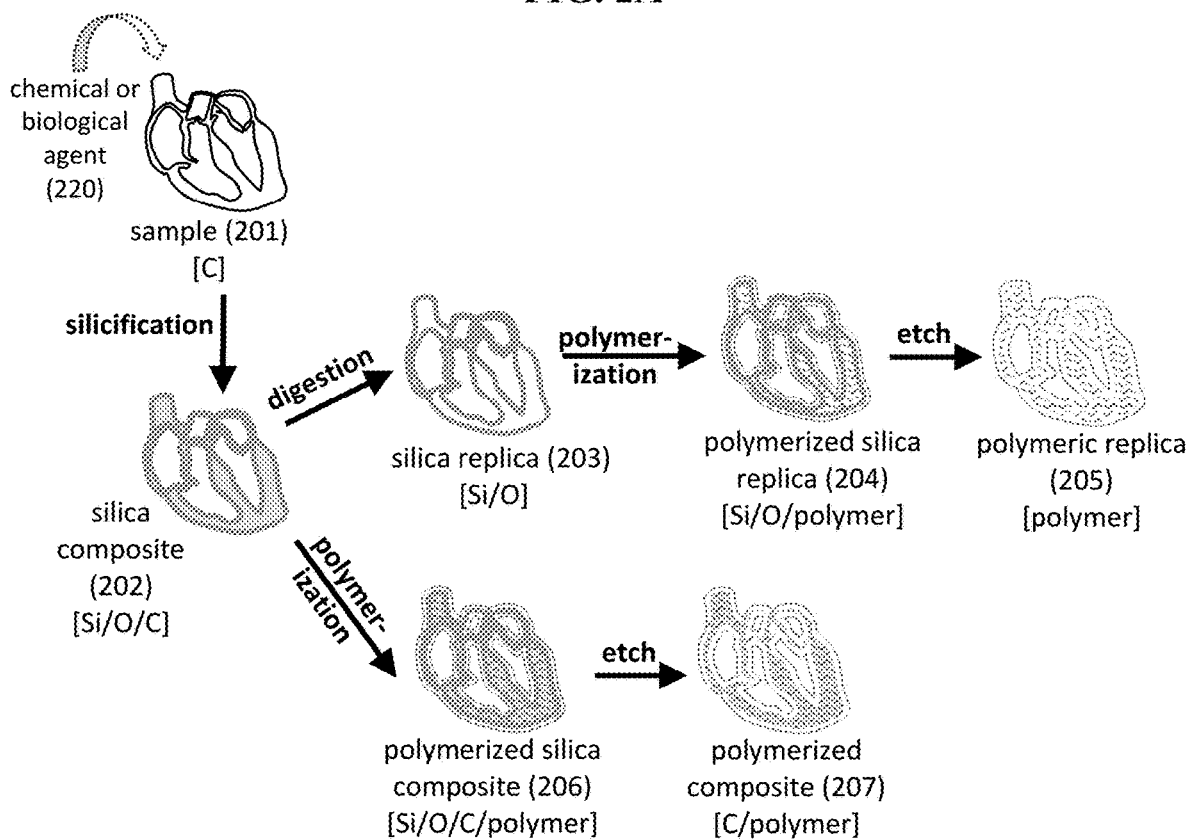

The silification process can produce different types of constructs. Exemplary constructs include a silica composite, a polymerized composite (e.g., a composite including a polymeric material and organic matter from the underlying biological sample, such as a polymerized composite or a polymerized silica composite), or a replica (e.g., a silica replica, a polymerized silica replica, a polymeric replica, etc.). As seen in FIG. 2B, the sample 201 can be any useful biological sample and includes carbon-based or organic matter [C], such as cellular components, cells, etc.

The sample 201 undergoes silification to provide a silica composite 202 including silicon, oxygen, and carbon [Si/O/C]. As employed herein, a silica composite is a structure including both the underlying organic matter of the sample, as well as one or more silica nanolayers deposited on an external and/or internal surface, or a portion thereof, of the sample.

Prior to silification, the sample 201 can be optionally treated with an agent 220 (e.g., any herein, such as a chemical or biological agent). The agent can be used to bind particular targets within the sample, to treat one or more different cell subtypes present in the sample (e.g., such as in a tumor cells within the sample), to encode a desired shape of the sample, to form pores on the surface of the sample and/or within the sample, to label the sample, etc. When the sample is treated in this manner, the latter silification process then provides a way to store this treated state or to further analyze various structural or biochemical changes that are induced by this treatment.

The silica composite 202 can be further processed, as seen in FIG. 2B. For instance, the underlying organic matter can be removed (e.g., by digestion). Alternatively, the underlying silica can be used as a template for deposition of a polymer precursor. In yet another alternative, the silica can be removed (e.g., by etching). These alternative composites and replicas are described below.

The silica composite generally includes an underlying organic structure, and the organic matter from this structure can be removed in any useful manner to provide an inorganic silica replica. In one instance, for the removal of organic matter, the silica composite 202 can undergo calcination, i.e., exposure to high temperature conditions to decompose organic matter (e.g., conditions such as a temperature of from about 500° C. to about 600° C. in air or an oxidative atmosphere). In another instance, organic matter can be removed by digestion, thereby providing a silica replica 203, which is predominantly silica [Si/O].

The silica replica can be employed as a template for polymeric precursors. For instance, exposure of the silica replica 203 to polymeric precursors and subsequent polymerization provides a construct having a polymer disposed upon that silica nanolayer. The resultant construct can be a polymerized silica replica 204 having silica and polymer [Si/O/polymer] but lacking organic matter. Optional etching of the silica then provides a construct having predominantly polymeric material, such as a polymeric replica 205 [polymer].

In another instance, the underlying organic matter can be retained. For this process, exposure of the silica composite 202 to polymeric precursors and subsequent polymerization provides a construct having a polymer disposed upon the silica nanolayer, in which organic matter underlies that silica nanolayer. The resultant construct can be a polymerized silica composite 206 having silica, organic matter, and a polymeric material [Si/O/C/polymer]. Optional etching of the silica then provides a construct having polymeric material and organic matter, such as a polymeric composite 207 [C/polymer].

Complex structures formed from other materials can be useful. For instance, such other materials can include metals (e.g., noble metals, metal carbides, metal oxides, etc.), semiconductor materials (e.g., silicon), ceramics, and magnetic materials. To form converted replicas having such materials, the silica composite's material can be converted into other materials by any useful reaction (e.g., displacement reactions, such as gas/solid or liquid/solid displacement reactions or metathetic gas/solid displacement reactions, such as with halide gases; oxidation reactions, such as oxidation-reduction displacement reactions; magnesiothermic reduction reactions; carbothermal reduction reactions; hydrothermal reactions; reactive metal reactions, such as with molten metals, including amalgams, oxides, and mixtures thereof; etc.). Exemplary reactions are described in Sandhage K H, "Materials 'alchemy': Shape-preserving chemical transformation of micro-to-macroscopic 3-D structures," *JOM* (*Journal of The Minerals, Metals & Materials Society* (*TMS*)) 2010 June; 62(6):32-43, which is incorporated herein by reference in its entirety.

Any of the composites or replicas herein can be further functionalized. In one instance, the composite or replica is functionalized by use of a silanizing agent (e.g., an agent having the structure of $(R^L)_3SiR^M$, where each $R^L$ is, independently, H, alkyl, hydroxyl, halo, or alkoxy, and $R^M$ is a functional moiety, as described herein). When a composite is employed, the silica surface of the composite can be used as a handle to support silane chemistry, thereby providing a silanized composite. Optionally, the silica surface can first be oxidized (e.g., by plasma) prior to silanization. In another instance, the composite or replica is functionalize by use of one or more particles (e.g., a nanoparticle, such as any herein), thereby providing a particle-coated composite. In yet another instance, the composite or replica includes a coating (e.g., such as by electroless deposition or sputter-coating, e.g., of a noble metal, such as Au, Ag, Pd, etc.; or by spin-coating with a polymer) with optional subsequent dissolution of the silicon (e.g., in KOH or NaOH), thereby providing a coated composite.

Any of the post-silification steps herein can be combined to form a useful composite or replica. For instance, the surface of a composite can be functionalized in any useful manner, and the underlying silica and/or organic matter can be transformed (e.g., into silicon, conductive carbon, a metal, a semiconductor, a ceramic, etc.) and/or removed (e.g., by etching silica or by digesting or calcinating organic matter). In a similar manner, any replica herein can be further functionalized (e.g., using a silane, a particle, a coating, etc.) to provide a functionalized replica. For instance, a polymeric replica can be functionalized with a poly(ethylene glycol) (e.g., to change the immunogenicity of the replica) and then optionally coated with a particle (e.g., to impart binding and/or fingerprinting capabilities of the replica).

Methods for Preparing Composites and Replicas

The constructs can be formed by employing any useful method that includes the silification process. In non-limiting embodiments, the method includes the step of providing a biological sample and the silification step of forming one or more silica nanolayers on and/or within the sample, thereby forming a silica composite. The method can include additional optional steps, as described herein. The silification step can include an immersion step of immersing the sample in a silicic acid solution, such as any herein; an incubation step of incubating the sample for a time sufficient to provide penetration of the silicic acid compounds into the tissue and/or its cells (e.g., for about three or more days, such as of from about one week to three weeks) at any useful temperature (e.g., room temperature, physiological temperature, etc.); and an optional replacement step of replacing or changing the silicic acid solution, as needed, to prevent silica condensation or gelation within the silicic acid solution. Furthermore, the volume of the silicic acid solution can be in excess of the volume of the sample, such as a volume ratio of from about 1:10 to about 1:100 for tissue:solution (e.g., from 1:10 to 1:50, such as about 1:20).

One optional step includes a treatment step in which the sample is treated with one or more agents before, during, and/or after the preparing step. The treatment step can be employed to understand how a particular agent (e.g., chemical or biological agent, such as any herein) affects the physical conformation or structure of the biological cell sample. For instance, if the tissue includes a cancerous growth, then the agent can be an anti-cancer agent; and the methods herein can be employed to form a silica composite or replica that accurately captures the location of the anti-cancer agent and, therefore, determines whether the anti-cancer agent effectively targets the cancerous cells. In another instance, the treatment step employs an agent that alters one or more physical characteristics of the silica nanolayer, such as thickness, porosity, continuity, etc. In yet another instance, the treatment step employs an agent that alters the shape of the sample, thereby providing a shape-encoded sample that can be silicified or processed (e.g., as described herein) to provide a composite or a replica. In one example, the shape-encoded sample includes a shape-encoded cell (e.g., a blood cell encoded by employing an amphipath).

Another optional step includes a sample preparation step. In particular, this step can include one or more additional sub-steps that assist in stabilizing and/or preparing the tissue, such as treating the tissue with one or more fixation agents, permeabilization reagents, etc. An exemplary sample preparation step includes an incubation step of incubating the biological sample source (e.g., an organism); a euthanization step of euthanizing the source; a fixation step of fixating the sample from the source with a fixation agent, such as any herein; and/or a rinse step of rinsing the fixed sample with a solvent, e.g., any aqueous solvent herein.

After forming the silica composite, one or more washing and/or drying steps can be conducted. In some embodiments, the washing step is conducted by employing successive wash conditions including an aqueous solvent, a mixture of an aqueous solvent with an organic solvent, and an organic solvent (e.g., an organic volatile solvent that assists in the drying step). Exemplary aqueous solvents include water (e.g., at any useful pH, such as of from about 1 to 4), a buffer (e.g., a phosphate buffered saline), an isotonic solution (e.g., about 300 mOsm/L), etc.; and exemplary organic solvents include an alcohol (e.g., ROH, such as methanol and ethanol), acetone, etc. An exemplary washing step includes a first wash step with an acidic aqueous solution (e.g., water at a pH of from about 0.5 to about 5, including any range described herein); a second wash step with a solvent mixture (e.g., of an acidic aqueous solution, such as that employed in the first wash step, and an organic solvent); and a third wash step with an organic solvent (e.g., any herein). The drying step can be conducted to dehydrate the silica composite, thereby forming a dry powder containing particles of silica composites.

The methods of the invention can be adapted to include any useful step performed in any useful sequence. One exemplary method includes a providing step and a sample preparation step, in which the treatment step can be performed after the providing step or performed as a sub-step within the sample preparation step. The method can further include a silification step, a washing step, and/or a drying step.

Various post-silification steps are optional, such as a calcination step, a carbonization step, an etch step, a digestion step, and an analysis/storage step. The calcination step can includes forming an inorganic silica by calcinating the silica composite. Any useful conditions can be employed to calcine the composite by decomposing the organic matter present in the underlying biological sample. Exemplary conditions include a high temperature (e.g., of from about 400° C. to about 600° C., including from 500° C. to 600° C.) and/or an oxidative atmosphere (e.g., in air).

The carbonization step can include forming a carbonized replica by carbonizing the silica composite. Any useful conditions can be employed to carbonize the composite by converting the organic matter present in the underlying biological sample into conductive carbon. Exemplary conditions include a high temperature (e.g., of from about 700° C. to about 1,100° C., including from 800° C. to 1,000° C. or about 900° C.) and/or a reductive or inert atmosphere.

The etching step can include use of a wet etchant (such as buffered hydrofluoric acid, potassium hydroxide, tetramethylammonium hydroxide, etc.), which includes immersing the composite or replica in an etchant in order to etch any remnant silica present within the replica.

The digestion step can include the use of any agent, e.g., acid, base, solvent, permeabilization reagent, etc., as well as combinations thereof, in order to remove organic matter from the composite.

The constructs of the invention can be further processed in any useful manner. For instance, the construct (e.g., any herein, including any composite or replica) can be treated with a halide gas/solid displacement reaction to transform the silica component into another metal oxide (e.g., employing titanium halide as a vapor to convert silica into titania, magnesium to convert silica to magnesium oxide, molten aluminum to promote reactive metal penetration and convert silica to aluminum oxide, as well as other reactions described in Sandhage K H, *JOM* (*Journal of The Minerals, Metals & Materials Society* (*TMS*)) 2010 June; 62(6):32-43, which is incorporated herein by reference in its entirety). Thus, any of the methods herein can include an optional conversion step, in which the base material of the composite is converted into another material by employing any useful reaction (e.g., any described herein).

In another instance, the construct can be further coated with one or more additional layers or particles, such as those formed from polymers, metals, conductive materials, semiconductor materials, etc., by any useful process (e.g., dip coating, spinning, low-pressure chemical vapor deposition, sputter coating, etc.). Thus, the methods herein can include an optional functionalization step, in which an inner or outer surface of a composite or replica is functionalized in any useful manner.

Silicic Acid Solutions

The methods and constructs herein employ a silicic acid solution, which provides one or more silicic acid compounds that form the silica nanolayer. In addition, the composition of the solution determines the kinetics of the silification process and, therefore, the structure of the silica nanolayer.

The silicic acid solutions of the invention can include any useful silicic acid. Exemplary silicic acids include tetraalkoxysilanes (e.g., $Si(OR)_4$, wherein each R is, independently, an optionally substituted alkyl, alkoxy, or alkoxyalkyl, as defined herein), such as tetramethoxysilane ($Si(OCH_3)_4$ or TMOS), tetraethoxysilane ($Si(OC_2H_5)_4$ or TEOS), tetra-n-propoxysilane ($Si(n-OC_3H_7)_4$), tetra-n-butoxysilane ($Si(n-OC_4H_9)_4$), and tetrakis(2-methoxyethoxy)silane ($Si(OCH_2CH_2OCH_3)_4$); oxo-acids, such as orthosilicic acid ($Si(OH)_4$), metasilicic acid ($Si(O)(OH)_2$), disilicic acid ($H_2Si_2O_5$), and pyrosilicic acid ($H_6Si_2O_7$); or organoalkoxysilanes (e.g., $R'Si(OR)_3$, wherein each of R' and R is, independently, an optionally substituted alkyl, aryl, alkaryl, alkenyl, and alkynyl as defined herein), such as methyltrimethoxysilane ($CH_3Si(OCH_3)_3$), methyltriethoxysilane ($CH_3Si(OC_2H_5)_3$), methyl tri-n-propoxysilane ($CH_3Si(n-OC_3H_7)_3$), phenyltriethoxysilane ($PhSi(OC_2H_5)_3$), and vinyltriethoxysilane ($CH_2=C(H)Si(OC_2H_5)_3$), as well as oligomeric (e.g., dimeric, trimeric, tetrameric, octomeric, etc.) forms thereof.

To inhibit gel formation (i.e., gelation of the silicic acid compounds), the silicic acid solution is sufficiently dilute and sufficiently acidic. The kinetics of gelation depends, in part, on the concentration of the silicic acid compound (and its hydrolyzed forms) and the pH of the solution. At low pH (e.g., less than pH of about 7), gelation is suppressed and occurs on long time scales. In addition, within this low pH regime (e.g., pH of about 3), the charge of orthosilicic acid $Si(OH)_4$ is neutral and, thus, interacts with other molecules by way of hydrogen bonding and other non-covalent interactions. At high pH (e.g., greater than or equal to a pH of 7), the kinetics of polymerization is predominated by maximal silica solubility and dissolution, and the silica components are ionized (i.e., charged).

In some embodiments of the present invention, the reaction conditions are selected to favor silicic acid penetration into cells and tissue structures and/or to favor silica nanolayer formation (rather than gel formation). In some embodiments, the reaction conditions are selected to promote a self-limited reaction (e.g., limited homopolymerization and/or limited gel formation). In other embodiments, the concentration of the silicic acid compound in the solution is of from about 10 mM to 800 mM of silicic acid (e.g., any silicic acid compound herein, such as from 10 mM to 500 mM, 10 mM to 300 mM, 10 mM to 200 mM, 10 mM to 100 mM, 10 mM to 50 mM, 25 mM to 800 mM, 25 mM to 500 mM, 25 mM to 300 mM, 25 mM to 200 mM, 25 mM to 100 mM, 25 mM to 50 mM, 50 mM to 800 mM, 50 mM to 500 mM, 50 mM to 300 mM, 50 mM to 200 mM, 50 mM to 100 mM, 75 mM to 800 mM, 75 mM to 500 mM, 75 mM to 300 mM, 75 mM to 200 mM, 75 mM to 100 mM, 100 mM to 800 mM, 100 mM to 500 mM, 100 mM to 300 mM, and 100 mM to 200 mM). In yet other embodiments, the pH of the silicic acid solution is of from about 0.5 to about 7 (e.g., from 0.5 to 6, 0.5 to 5, 0.5 to 4, 0.5 to 3, 0.5 to 2, 0.5 to 1, 1 to 7, 1 to 6, 1 to 5, 1 to 4, 1 to 3, 1 to 2, 2 to 7, 2 to 6, 2 to 5, 2 to 4, 2 to 3, 3 to 7, 3 to 6, 3 to 5, and 3 to 4).

The solution can be formed with any useful solvent, such as an aqueous solvent including water (e.g., deionized water), a buffer (e.g., a phosphate buffer, a citric acid-$Na_2HPO_4$ buffer, a citric acid-sodium citrate buffer, a sodium acetate-acetic acid buffer, etc.), or a saline (e.g., phosphate buffered saline, Ringer's saline, Tris-buffered saline, borate-buffered saline, Hank's balanced salt solution, standard saline citrate, etc.) at any useful pH, such as any described herein. The pH of the solvent can be obtained by employing any useful acid or base. In certain embodiments, the aqueous solution includes an acid, such as one or more of hydrogen chloride, acetic acid, nitric acid, trifluoroacetic acid, etc.

In some instances, the solution is an isotonic solution (e.g., about 300 mOsm/L). Isotonicity can be maintained with any useful ion (e.g., sodium, potassium, calcium, chloride, lactate, etc.) or salt, such as sodium chloride, calcium chloride, potassium chloride, sodium lactate (e.g., 0.90% w/v of NaCl). In yet other instances, the solution is an acidic isotonic solution including any useful ion, solvent, and/or acid (e.g., any described herein).

Polymeric Precursors

Any useful polymeric precursor, or a combination of two or more different precursor, can be employed to assembly any construct herein (e.g., a polymerized silica composite, a polymerized composite, a polymeric silica replica, or a polymeric replica). The resultant construct can have any useful polymer (e.g., a hydrogel, a sol-gel, etc.).

In some embodiments, the polymeric precursor is $L^1$-$R^m$-$L^2$, in which $R^m$ is any useful chemical group (e.g., a monomer) and each of $L^1$ and $L^2$ is, independently, a reactive group (e.g., a functional group that is one of a cross-linker group, a binding group, or a click-chemistry group, such as any described herein), and in which each of $L^1$ and $L^2$ can be the same or different. In other embodiments, each of $L^1$ and $L^2$ is chosen to be one of a reaction pair (e.g., a cross-linker reaction pair, a binding reaction pair, or a click-chemistry reaction pair, such as any described herein). In yet other embodiments, each of $L^1$ and $L^2$ has any useful valency to provide any useful number of covalent bonds. For instance, each of $L^1$ and $L^2$, independently, can be bivalent (e.g., a bivalent $L^1$, thereby allowing for a first bond between $L^1$ and $R^m$ and a second bond to be formed between $L^1$ and $L^2$ present on different precursors), trivalent (e.g., a trivalent $L^1$, thereby allowing for a first bond between $L^1$ and $R^m$ and two other bonds to be formed between $L^1$ and other reactive groups, such as $L^2$ present on the same precursor or different precursors), tetravalent, pentavalent, multivalent (i.e., greater than bivalent), etc.

Exemplary reactive groups include any chemical group configured to form a bond. In general, a first chemical group reacts with a second chemical group to form a bond (e.g., a covalent bond), in which the first and second chemical groups form a reactive pair.

In one instance, the reactive group is a cross-linker group. In another non-limiting instance, the reactive pair is a cross-linker reaction pair, which includes a first cross-linker group and a second cross-linker group that reacts with that first cross-linker group. Exemplary cross-linker groups and cross-linker reaction pairs include those for forming a covalent bond between a carboxyl group (e.g., —$CO_2H$) and an amino group (e.g., —$NH_2$); or between a phospho group (e.g., —$P(O)(OH)_2$) and an amino group (e.g., —$NH_2$), such as 1-ethyl-3-(3-dimethylaminopropyl)carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., —NH$_2$) and a thymine moiety, such as succinimidyl-[4-(psoralen-8-yloxy)]-butyrate (SPB); a hydroxyl group (e.g., —OH) and a sulfur-containing group (e.g., free thiol, —SH, sulfhydryl, cysteine moiety, or mercapto group), such as p-maleimidophenyl isocyanate (PMPI); between an amino group (e.g., —NH$_2$) and a sulfur-containing group (e.g., free thiol, —SH, sulfhydryl, cysteine moiety, or mercapto group), such as succinimidyl 4-(p-maleimidophenyl)butyrate (SMPB) and/or succinimidyl 4-(N-maleimidomethyl)cyclohexane-1-carboxylate (SMCC); between a sulfur-containing group (e.g., free thiol, —SH, sulfhydryl, cysteine moiety, or mercapto group) and a carbonyl group (e.g., an aldehyde group, such as for an oxidized glycoprotein carbohydrate), such as N-beta-maleimidopropionic acid hydrazide-trifluoroacetic acid salt (BMPH), 3-(2-pyridyldithio)propionyl hydrazide (PDPH), and/or a 3-(2-pyridyldithio)propionyl group (PDP); and between a maleimide-containing group and a sulfur-containing group (e.g., free thiol, —SH, sulfhydryl, cysteine moiety, or mercapto group). Yet other cross-linkers include those for forming a covalent bond between two or more unsaturated hydrocarbon bonds, e.g., mediated by radical polymerization, such as a reaction of forming a covalent bond between a first alkene group and a second alkene group (e.g., a reaction between acrylate-derived monomers to form a polyacrylate, polyacrylamide, etc.).

In another instance, the reactive group is a binding group. In another non-limiting instance, the reactive pair is a binding reaction pair, which includes a first binding group and a second binding group that reacts with that first binding group. Exemplary binding groups and binding reaction pairs include those for forming a covalent bond between biotin and avidin, biotin and streptavidin, biotin and neutravidin, desthiobiotin and avidin (or a derivative thereof, such as streptaviding or neutravidin), hapten and an antibody, an antigen and an antibody, a primary antibody and a secondary antibody, and lectin and a glycoprotein.

In yet another instance, the reactive group is a click-chemistry group. In another non-limiting instance, the reactive pair is a click-chemistry reaction pair, which includes a first click-chemistry group and a second click-chemistry group that reacts with that first click-chemistry group. Exemplary click-chemistry groups include, e.g., a click-chemistry group, e.g., one of a click-chemistry reaction pair selected from the group consisting of a Huisgen 1,3-dipolar cycloaddition reaction between an alkynyl group and an azido group to form a triazole-containing linker; a Diels-Alder reaction between a diene having a 4π electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a 2π electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group.

Exemplary monomer groups include any useful subunit, which when repeated, provides a polymer having any useful property. Exemplary monomer groups are those including an ethylene glycol group, e.g., —OCH$_2$CH$_2$—, including a poly(ethylene glycol) (PEG) group —(OCH$_2$CH$_2$)$_n$—, a four-arm PEG group (such as C(CH$_2$O(CH$_2$CH$_2$O)$_n$—)$_4$ or C(CH$_2$O(CH$_2$CH$_2$O)$_n$CH$_2$-)$_4$ or C(CH$_2$O(CH$_2$CH$_2$O)$_n$CH$_2$CH$_2$-)$_4$ or C(CH$_2$O(CH$_2$CH$_2$O)$_n$CH$_2$CH$_2$NHC(O)CH$_2$CH$_2$-)$_4$C(CH$_2$O(CH$_2$CH$_2$O)$_n$CH$_2$C(O)O—)$_4$), an eight-arm PEG group (such as —(OCH$_2$CH$_2$)$_n$O[CH$_2$CHO((CH$_2$CH$_2$O)$_n$—)CH$_2$O]$_6$(CH$_2$CH$_2$O)$_n$ or —CH$_2$(OCH$_2$CH$_2$)$_n$O[CH$_2$CHO((CH$_2$CH$_2$O)$_n$CH$_2$—)CH$_2$O]$_6$(CH$_2$CH$_2$O)$_n$CH$_2$— or —CH$_2$CH$_2$(OCH$_2$CH$_2$)$_n$O[CH$_2$CHO((CH$_2$CH$_2$O)$_n$CH$_2$CH$_2$—)CH$_2$O]6(CH$_2$CH$_2$O)$_n$CH$_2$CH$_2$— or R(O(CH$_2$CH$_2$O)$_n$—)$_8$ or R(O(CH$_2$CH$_2$O)$_n$CH$_2$-)$_8$ or R(O(CH$_2$CH$_2$O)$_n$CH$_2$CH$_2$-)$_8$, in which R includes a tripentaerythritol core), or a derivatized PEG group (e.g., methyl ether PEG (mPEG), a propylene glycol group, etc.); including dendrimers thereof, copolymers thereof (e.g., having at least two monomers that are different), branched forms thereof, start forms thereof, comb forms thereof, etc., in which n is any useful number in any of these (e.g., any useful n to provide any useful number average molar mass $M_n$).

Exemplary polymeric precursors can include a poly(ethylene glycol) group (e.g., a multivalent poly(ethylene glycol) precursor having a reactive functional group, such as an amino group, an ester group, an acrylate group, a hydroxyl group, a carboxylic acid group, etc.), such as eight arm-PEG amine (8-arm PEG-NH$_2$, e.g., catalog nos. PSB-811, PSB-812, or PSB-814 available from Creative PEGWorks, Chapel Hill, N.C.) or an eight-arm PEG succinimidyl ester (such as 8-arm PEG succinimidyl NHS ester or 8-arm PEG-SCM (succinimidyl carboxyl methyl ester), e.g., catalog nos. PSB-841, PSB-842, or PSB-844 available from Creative PEGWorks) or an eight-arm PEG vinylsulfone or an eight-arm PEG hydroxyl or a linear PEG thiol or a linear PEG hydroxyl or poly(ethylene glycol diacrylate) (PEG-DA) or triethylene glycol acrylate (TEGA) or 2-carboxyethyl acrylate (CEA) or 2-hydroxyethylacrylate (HEA), as well as copolymers thereof and/or combinations thereof; an amino acid (e.g., a poly(amino acid) precursor or a protein, such as a poly(lysine) precursor, a poly(arginine) precursor, lysozyme, avidin, or albumin); a glycerol group (e.g., a poly(glycerol) precursor); a vinyl group (e.g., a poly(vinyl) precursor or a poly(vinyl alcohol) precursor); a hydroxyacid group (e.g., a poly(lactic acid) precursor, a poly(glycolic acid) precursor, or a poly(lactic-co-glycolic acid) precursor); an acrylate group (e.g., a poly(acrylic acid) precursor or a poly(methacrylic acid) precursor); a silyl ether group (e.g., a poly(silyl ether) precursor); an olefin group (e.g., a poly(acetylene) precursor); and/or an aromatic group (e.g., a poly(pyrrole) precursor, a poly(aniline) precursor, or a poly(thiophene) precursor).

Polymeric precursors can be employed in any useful manner to construct a polymeric layer. In one instance, such precursors are deposited on a silica nanolayer and then directly polymerized (e.g., by use of any useful reaction condition, including thermal heating, use of a cross-linking agent (e.g., glutaraldehyde or any other fixative agent described herein), photopolymerization by employing one or more photoinitiators (e.g., such as an aryl ketone, including Darocur™ 1173 (2-hydroxy-2-methyl-1-phenyl-propan-1-one) or 1-hydroxycyclohexyl phenyl ketone (HCPK)); or an azo initiator, such as VA-044 (2,2'-azobis[2-(2-imidazolin-2-yl)propane]dihydrochloride)). After polymerization, the resultant constructs can be further treated (e.g., hydrated, swelled, digested, sterilized, lysed, dialyzed, coated, conjugated, and/or functionalized, such as with an agent or a protein, etc.).

In another instance, precursors are deposited by way of layer-by-layer assembly (e.g., in which a first polyelectrolyte is deposited as a first layer on the silica nanolayer and then a second polyelectrolyte is deposited upon the first layer, where the first polyelectrolyte can have a first charge and the second polyelectrolyte possesses a second charge that is opposite of the first charge). Exemplary precursors include a first polyelectrolyte that is cationic and a second polyelectrolyte that is anionic (e.g., in which the silica surface has an anionic surface charge); or a first polyelectrolyte that is anionic and a second polyelectrolyte that is cationic (e.g., in which the silica surface is then treated to have a cationic surface charge, e.g., by use of an amino-terminated silane). Other useful polymer deposition techniques include sol-gel processing, dip coating, ink jet printing, spraying, spin-coating, and perfusion.

Other polymeric precursors include poly(anionic) polymers, such as alginate (ALG), albumin (including bovine serum albumin (BSA)), dextran (e.g., dextran sulfate), heparin (HEP), hyaluronan (HA), pectin (PEC), poly(acrylic acid) (PAA), poly(glutamic acid) (PGA, including poly(L-glutamic acid) (PLGA)), poly(methacrylic acid) (PMAA), poly(styrene sulfonate) (PSS, including copolymers thereof, such as poly(4-styrenesulfonic acid-co-maleic acid) (PSS-MA)), poly(vinyl sulfate) (PVS), and poly(vinyl sulfonate) (PVSO); and well as poly(cationic) polymers, such as chitosan (CHT), lysozyme (LYS), poly(allylamine), including poly(allylamine hydrochloride) (PAH), poly(diallyldimethylammonium halide) (PDADMA, including copolymers thereof, such as PDADMA chloride and N-methyl-N-vinylformamide (NMVF)), poly(arginine) (including poly(L-arginine)), poly(2-(dimethylamino)ethyl methacrylate) (PDMAEMA), poly(ethyleneimine) (PEI), and poly(lysine) (PL, including poly(L-lysine) (PLL)), in which a poly(anionic) polymer and a poly(cationic) polymer forms a polyelectrolyte pair that interact by way of charge-based interactions.

Other polymeric precursors include those that can be polymerized to form a hydrogel. Exemplary, non-limiting polymeric precursors include PEG macromers (e.g., having vinylsulfone, acrylate, hydroxyl, and/or maleimide reactive groups on branched, multiarm PEG macromers), bifunctional PEGs having reactive groups (e.g., thiol end groups), acrylamides (e.g., any described herein), etc. Other hydrogel polymeric precursors are described in U.S. Pat. Appl. Pub. Nos. 2010/0055733 and 2015/0144490, each of which is incorporated herein by reference in its entirety.

Some polymeric precursors can interact (e.g., in a layer-by-layer assembly) by way of hydrogen-bonding interactions (e.g., in which an interactive pair can include a hydrogen bonding donor and a hydrogen bonding acceptor); charge transfer interactions; host-guest interactions; biological binding interactions; coordination chemistry interactions; stereocomplexation; covalent bonding interactions; and surface sol-gel process interactions. Exemplary polymeric precursors can include those described in Borges J et al., "Molecular interactions driving the layer-by-layer assembly of multilayers," *Chem. Rev.* 2014; 114:8883-942, which is incorporated herein by reference in its entirety.

In yet another instance, polymeric precursors are employed to form multilayers upon the silica nanolayer. Such multilayers can be composed of the same precursor, different precursors, or alternating layers of a plurality of different precursors.

Synthetic Constructs

The present invention also related to synthetic constructs formed by way of silicification and subsequent polymerization. An exemplary synthetic construct can include a construct (e.g., any described herein, such as a polymeric replica), an oxygen carrier, and optionally one or more endogenous or exogenous oxygen-binding molecules loaded within or in proximity to the construct.

The material properties of the synthetic construct can be optimized in any useful manner. For instance, the synthetic construct can be optimized to perform as an artificial blood substitute, in which the shape of the construct can be determined by using a red blood cell as the initial biological sample upon which to form a silica template. In addition, polymeric precursors can be chosen to mimic the rheology, tensility, and/or swellability that would be beneficial in blood transport and/or biological function in vivo.

The synthetic construct can be further functionalized. In one non-limiting instance, the construct can include a coating (e.g., a lipid layer coating, a polymeric coating, etc.) surrounding a periphery of the construct. Exemplary non-limiting coatings can include a phospholipid monolayer, a lipid monolayer, a lipid bilayer, a lipid multilayer, one or more lipopolymers or block copolymers, one or more pegylated lipids, a glycoprotein (e.g., CD47), and/or a sterol (e.g., cholesterol).

In another non-limiting instance, a particle (e.g., a nanoparticle) or reactive group (e.g., a binding group, click-chemistry group, a cross-linker group, such as any described herein) is disposed within the construct or on a surface of the construct. Such particles and reactive groups may be useful for detection of the construct, active withdrawal of the construct (e.g., during dialysis), etc. Exemplary particles include magnetic particles, fluorescent particles, etc.

The synthetic construct can be provided within any useful solvent (e.g., a solution including a synthetic construct that is solvated within a solvent). In addition, any useful solvent can be provided (e.g., sealed) within the synthetic construct and/or tethered to a surface of the synthetic construct. Non-limiting solvents include a buffer, an oxygen carrier, or an aqueous solution, as well as emulsions thereof. Exemplary oxygen carriers includes those having a perfluorinated group, such as a perfluoroalkyl group, a perfluoroalkylene group, a perfluoroalkyleneoxy group, or a perfluoroalkoxy group, including perfluorodecalin ($C_{10}F_{18}$), perfluorocarbon, perfluoro(tert-butylcyclohexane), $C_{10}F_{20}$, perfluorotributylamine, dodecafluoropentane, perfluorooctyl bromide ($C_8F_{17}Br$), perfluorodecyl bromide ($C_{10}F_{21}Br$), perfluorodichlorooctane ($C_8F_{16}C_{12}$), as well as emulsions thereof (e.g., including one or more phospholipids, triglycerides, etc.).

One or more endogenous or exogenous oxygen-binding molecules can be loaded within the polymeric replica and/or provided in proximity to the replica (e.g., tethered to an outer surface of the replica or to a coating disposed upon the replica). Exemplary oxygen-binding molecules can include proteins, such as hemoglobin, porphyrin, or a modified form, a cross-linked form, and/or a recombinant form thereof (e.g., cross-linked hemoglobin (e.g., cross-linkages formed between subunits of a tetrameric hemoglobin molecule), polymerized hemoglobin (e.g., a plurality of hemoglobin molecules linked together, such as glutaraldehyde hemoglobin, raffinose-linked hemoglobin), conjugated hemoglobin (e.g., surface-modified hemoglobin molecule, such as pegylated (PEG-conjugated) hemoglobin, polyoxyethylene-conjugated hemoglobin, maleimide PEG-conjugated) hemoglobin), pegylated hemoglobin, dextran-stabilized hemoglobin, heme protein, protected porphyrin, hemerythrin, hemocyanin, methemoglobin, pyridoxylated polymerized hemoglobin, nitroxide-conjugated hemoglobin, nitroxylated pegylated hemoglobin, nitrosylated hemoglobin, and nitrosylated pegylated hemoglobin, vesicle-encapsulated hemoglobin. The protein may be from any useful source (e.g., a mammalian source, such as a human or bovine source) or may be recombinantly manufactured. Further exemplary oxygen carriers and oxygen-binding molecules are described in Palmer A F et al., "Blood substitutes," *Annu. Rev. Biomed. Eng.* 2014; 16:77-101 and Tao Z et al., "Microparticle, nanoparticle, and stem cell-based oxygen carriers as advanced blood substitutes," *Trends Biotechnol.* 2014; 32(9):466-73, each which is incorporated herein by reference in its entirety.

Additional agents may be disposed on a surface of the construct and/or disposed within a solution including the construct. Exemplary agents include a stabilizer (e.g., albumin, lechitin), an antibiotic, a vitamin, a nutrient, a volume expander (e.g., dextran (in water or saline), saline, sodium chloride solution, Ringer's lactate, Ringer's acetate, albumin, pegylated albumin, polymerized albumin, fresh frozen plasma, hydroxyethyl starch, gelatin, alginate), and/or a salt.

Further Uses

The present invention also relates to use of optical microscopy, including expansion microscopy. In one instance, constructs can be formed to include optically clear polymer or polymeric precursors, thereby allowing optical microscopy to be used to probe underlying biological structure that is covalently anchored by way of silification to provide a silica template and polymerization to provide a polymerized composite or polymeric replica. In one non-limiting instance, cellular material (e.g., optically opaque material, such as lipids, tissue, proteins, etc.) can be digested, extracted, proteolysed, lysed, dialyzed, and/or removed in any useful manner (e.g., as described herein). Optionally, if the polymeric precursors are chosen to provide a swellable polymer network (e.g., by use of hydrogel precursors that, upon polymerization, provides a swellable hydrogel), then the resultant composite can be physically expanded (e.g., hydrated) to provides a physically magnified construct.

Exemplary optically clear polymeric precursors can include an acrylate group (e.g., sodium acrylate, acrylamide, bisacrylamide, N,N'-methylenebisacrylamide), in the optional presence of a fixation agent (e.g., paraformaldehyde, formaldehyde, glutaraldehyde, etc.) and/or a photoinitiator (e.g., any herein, including an azo initiator, such as VA-044). Additional methods and precursors are provided in Chung K et al., "Structural and molecular interrogation of intact biological systems," *Nature* 2013; 497:332-337 with Supplementary methods (2 pp.) and U.S. Pat. Appl. Pub. No. 2015/0144490, each which is incorporated herein by reference in its entirety.

Biological Sample

Constructs can be formed from any useful biological sample, such as a cell sample, a tissue sample, or a population of cells. Exemplary samples include an organism (e.g., a non-viral organism, a mammalian organism, a vertebrate organism, a unicellular organism, a multicellular organism, a prokaryote, or a eukaryote), an embryo (e.g., a non-human embryo), an organ (e.g., brain, cochlea, eye, heart, intestines, kidney, liver, lung, ovary, pancreas, skin, spleen, stomach, and testis), a graft (e.g., an autograft, an allograft, an isograft, or a xenograft), a tissue culture, a tissue biopsy, a tissue section from any useful source (e.g., a mammalian source, such as a non-human mammalian source, a plant source, a fungal source, a microorganism source, a bacterial source, a viral source, etc.), a cell (e.g., a red blood cell, a neuron, and/or a glial cell), a multicellular sample, a soft tissue sample, a printed protein structure (e.g., a protein hydrogel, such as an albumin hydrogel, avidin hydrogel, lysozyme hydrogel, etc.), a population of cells, chondral tissue, cartilage, tendon(s), ligament(s), vertebral disc(s), soft tissue (e.g., tendon, ligament, blood vessel, skin, articular cartilage, etc.), osteochondral tissue, islet tissue, osteogenic tissue, neural tissue, skin, bone tissue, bone marrow, adipose tissue, fibroblast(s), muscle tissue, blood, blood cells (e.g., a red blood cell, a white blood cell (e.g., a neutrophil, an eosinophil, a basophil, a lymphocyte, or a monocyte), a hematopoietic stem cell, a platelet, a peripheral blood stem cell, etc.), a protein (e.g., a functional protein, hemoglobin, etc.), corneal tissue, ocular lens, meniscus, hair, striated muscle, smooth muscle, cardiac muscle, connective tissue, and stem cells. The sample can be obtained from any useful subject or source (e.g., a human subject, a non-human subject, a mammalian subject, an animal subject, etc.).

In yet other embodiments, the constructs further includes any cellular component. Exemplary cellular components include a virus, a protein, a nucleic acid (e.g., DNA, RNA, as well as hybrids and duplexed forms thereof), a lipid particle, a biomolecule, a lipid, a lipid vesicle, a polysaccharide, an organelle, and a cytoskeletal filament.

In particular embodiments, the methods and constructs herein employ one or more cells, as defined herein. Surprisingly, the methods herein can accurately preserve the shape of cells obtained from soft tissue sources. In one instance, the soft tissue source has an ultimate strength (i.e., the breaking strength of a material under different modes of loading, such as tensile, compressive, torsional, or bending modes) less than that of bone (e.g., where the soft tissue source has an ultimate tensile strength less than about 135 MPa and/or an ultimate compressive strength less than about 200 MPa). In other instance, the soft tissue source has an ultimate tensile strength of from about 0.1 MPa to about 110 MPa. Exemplary ultimate tensile strength values include those for urinary bladder (about 0.1 to 0.4 MPa), artery (about 0.1 to 0.9 MPa), aorta (about 0.3 to 2.5 MPa), skin (about 1 to 20 MPa), liver (about 1.8 to 3 MPa), spinal or cranial dura (about 2 to 5 MPa), cartilage (about 3 to 40 MPa), ligament (about 50 to 100 MPa), and tendon (about 50 to 100 MPa). Methods for evaluating ultimate strength, as well as other exemplary values, are provided in Brunon A et al., "Mechanical characterization of liver capsule through uniaxial quasi-static tensile tests until failure," *J. Biomech.* 2010; 43:2221-7; Holzapfel G A et al., "Biomechanics of soft tissue," *Biomech Preprint Series*, paper no. 7, Graz University of Technology, Austria, November 2000 (15 pp.); and Pal S, "Mechanical properties of biological materials," in *Design of Artificial Human Joints & Organs*, Springer Science+Business Media, New York, N.Y., 2014, pp. 23-40, each of which is incorporated herein by reference in its entirety.

Biological components of the sample can be removed in any useful manner. For instance, biological components can be digested (e.g., by use of an acid (e.g., HF, $HNO_3$, etc.) and/or a permeabilization reagent (e.g., any herein, including SDS) and/or extracted (e.g., by use of a permeabilization reagent, hydrophobic organic solubilization, electrophoresis, etc.).

Agents, Including Fixation Agents, Chemical Agents, and/or Biological Agents

The biological sample can be treated with one or more fixation agents. The fixation agent can include any useful agent or compound configured to form a bond (e.g., a covalent bond) between two reactive groups (e.g., a carboxyl group and an amino group or a phospho group and an amino group). Exemplary fixation agents include a chemical fixative (e.g., formaldehyde, paraformaldehyde, glutaraldehyde, formalin, acetone, isopropanol, ethanol, and/or methanol) or a cross-linker (e.g., any cross-linker group or cross-linker reaction pair described herein), as well as combinations thereof. Treatment with a fixative reagent can be followed by a rinse step (e.g., with any useful solvent, such as any aqueous solvent described herein).

The biological sample can be treated with one or more permeabilization reagents. The permeabilization reagents can include any useful agent or compound configured to permeabilize cell membranes, or portions thereof. Exemplary permeabilization reagents include a surfactant, such as Triton™ X-100 (e.g., polyethylene glycol p-(1,1,3,3-tetramethylbutyl)-phenyl ether), sodium dodecyl sulfate (SDS), Tergitol-type NP-40 (nonyl phenoxypolyethoxylethanol), and polysorbate 20 (Tween 20); an alcohol, such as methanol; a solvent (e.g., acetone or acetic acid); a glycoside, such as saponin or digitonin; a protease, such as proteinase K; or an exotoxin, such as streptolysin O.

The biological sample can be treated with one or more chemical or biological agents. Exemplary agents (e.g., chemical or biological reagents) include a therapeutic agent, e.g., a drug, a pro-drug, a vitamin, an antibody, a protein, a hormone, a growth factor, a cytokine, a steroid, an inhibitor (e.g., a kinase inhibitor), an anti-cancer agent, a fungicide, an anti-microbial, an antibiotic, etc.; a morphogen; an enzyme; a nucleic acid or a polynucleotide, including double stranded, single stranded, multiplexed, RNA, DNA, siRNA, chimeric, etc., forms thereof; a toxin, e.g., a bacterial protein toxin; a peptide, e.g., an antimicrobial peptide, a fibronectin motif (e.g., represented by the amino acid sequence RGD), or a collagen motif (e.g., represented by the amino acid sequence DGEA, SEQ ID NO: 1); an antigen; an antibody; a detection agent (e.g., a particle, such as a conductive particle, a microparticle, a nanoparticle, a quantum dot, a latex bead, a colloidal particle, a magnetic particle, a fluorescent particle, etc.; or a dye, such as a fluorescent dye, a luminescent dye, a chemiluminescent dye, a colorimetric dye, a radioactive agent, an electroactive detection agent, etc.); a label (e.g., a quantum dot, a nanoparticle, a microparticle, a barcode, a fluorescent label, a colorimetric label, a radio label (e.g., an RF label or barcode), avidin, biotin, a tag, a dye, a marker, an electroactive label, an electrocatalytic label, and/or an enzyme that can optionally include one or more linking agents and/or one or more dyes); a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), and/or an enzyme (e.g., that reacts with one or more markers, such as any described herein)); as well as combinations thereof.

In some embodiments, the biological sample is treated with an agent to alter its geometry or morphology. For instance, the sample can be treated with an agent that forms pores within a lipid layer, e.g., an antibiotic, a bacterial protein toxin, a cell permeabilizing agent, or an antimicrobial peptide that forms pores within lipid layers of cells, such as a bacterial cell. In another instance, the sample is treated with an agent that promotes cross-linking of various receptors present on a cell, such as an antigen that binds to receptors in an immunological cell (e.g., a mast cell). In yet another instance, the sample is treated with an agent that promotes cytoskeletal rearrangement within a cell, such as by employing a GTP-ase inhibitor and/or growth factors that promote actin rearrangement.

In another instance, the sample is treated with an amphipath, which is a chemical compound displaying both hydrophobic and hydrophilic chemical functional groups. In addition, such amphipaths can be positively charged (cationic), negatively charged (anionic), or neutral at a particular pH (e.g., a pH of 7). Without wishing to be limited by mechanism, such amphipaths localize preferentially into different regions of a lipid layer, in which more cationic amphipaths insert into more negatively charged regions of the lipid layer and more anionic amphipaths insert into more positively charged regions of the lipid layer. This molecular interaction results in a geometric change on a cellular level, such that the amphipath-treated lipid layers will preferentially form cup-shaped cells, crenated cells, spherical cells, etc. based on the cationic or anionic nature of the amphipath agent. Thus, amphipaths can be employed to provide shape-encoded cells, composites, and replicas.

Exemplary amphipaths include cationic amphipaths (e.g., a phenothiazine (e.g., chlorpromazine, methochlorpromazine, promazine, promethazine, thioridazine, trifluoperazine, triflupromazine, and salts thereof), an antihistamine (e.g., pheniramine, brompheniramine, or bamipine), a local anesthetic (e.g., procaine, lidocaine, dibucaine, stadacaine, tetracaine, and salts thereof), N,N-dimethylaminoethyl benzoate, N,N-diethylaminoethyl benzoate, N,N-diethyl-3-(4-nitrophenyl)propan-1-amine (HK-27), N,N,N-triethyl-4-nitrobenzenepropanaminium (HK-25), lidocaine N-methyl hydrochloride (QX-222), chloroquine, reserpine, prenylamine, verapamil, or salts thereof); anionic amphipaths (e.g., free fatty acids, barbiturates, benzoates (e.g., gentisate or salicylate), bile acids, alkyl sulfonates, alkylpyridinium chlorides, ethacrynic acid, 2,3-dinitrophenol, trinitrophenol, dipyridamole, or salts thereof); neutral amphipaths (e.g., lysolecithin, saponine, etc.); detergents; surfactants (e.g., Triton-X 100 or octylammonium chloride); lipids (e.g., a phospholipid such as phosphatidylcholine or a lysophospholipid such as lysophosphatidylcholine); fatty acids (e.g., a polyunsaturated fatty acid such as arachidonic acid); as well as surface active agents and surface active drugs (e.g., those described in Schreier S et al., "Surface active drugs: self-association and interaction with membranes and surfactants. Physicochemical and biological aspects," *Biochim. Biophys. Acta* 2000 November; 1508(1-2):210-34 and Wong P, "A basis of echinocytosis and stomatocytosis in the disc-sphere transformations of the erythrocyte," *J. Theor. Biol.* 1999 Feb. 7; 196(3):343-61, each of which is incorporated herein by reference in its entirety).

Other alterations to the intracellular or extracellular environment can induce a change in shape or geometry. For instance, such alterations can include a change in salt concentration, change in pH, change in cholesterol concentration within the membrane, and change in ATP concentration. Cup-shaped red blood cells can be induced by employing low salt, low pH, and/or cholesterol depletion conditions. In contrast, crenate red blood cells can be induced by employing high salt, high pH, cholesterol enrichment, and/or ATP depletion conditions. Such conditions and environments can be provided to the sample with any useful agent. Exemplary agents include an acid, a base, or a buffer (e.g., to change pH conditions); exogenous salts or ions, such as monovalent or divalent salts including cobalt, nickel, calcium, magnesium, or manganese ions with an optional ionophore (e.g., to change intracellular or extracellular salt conditions); exogenous cholesterol (e.g., to increase cholesterol concentration within the lipid membrane); and/or a cholesterol binding agent (e.g., to bind and remove cholesterol from membranes, such as by employing a cyclodextrin derivative, e.g., methyl-β-cyclodextrin).

Chemical and biological agents can also be employed with a composite or a replica (i.e., after the biological sample has been silicified and then either calcined, carbonized, etched, transformed, converted, functionalized, etc.).

Such agents can be used to introduce new functional groups to the composite or replica. Functional groups can impart any useful property, such as binding specificity, hydrophobicity, hydrophilicity, biocompatibility, non-immunogenicity, detectability, etc.

In one instance, the composite or replica can be functionalized with one or more silanizing agents to modify surface characteristics. For instance, if the silanizing agent has a hydrophobic moiety, then the composite or replica can be rendered hydrophobic upon functionalizing with that agent. Exemplary silanizing agents include silazane (e.g., hexamethyldisilazane (HMDS)), haloalkylsilane (e.g., methyltrichlorosilane, trichlorocyclohexylsilane, dichlorodimethylsilane, dichloroethylsilane, bromotrimethylsilane, or chlorotrimethylsilane), haloarylsilane (e.g., fluorotriphenylsilane), trialkylsilylsilane (e.g., chlorotris(trimethylsilyl)silane), and silanol (e.g., 2-(trimethylsilyl)ethanol). Other silanizing agents include an agent having the structure of $(R^L)_3SiR^M$ or $R^LSi(R^M)_3$ or $R^LSi(SiR^M)_3$ or $(R^L)_2R^MSi$-L-$SiR^M(R^L)_2$, where each of $R^L$ is, independently, H, optionally substituted alkyl, hydroxyl, hydroxyalkyl, halo, haloalkyl, alkoxy, or aryl; each of $R^M$ is, independently, a functional moiety, such as optionally substituted alkyl, haloalkyl, hydroxyalkyl, alkenyl, alkoxy, aryl, alkaryl, heterocyclyl, heteroaryl, cycloalkyl, alkcycloalkyl, amino, aminoalkyl, or amido, as defined herein; L is a linker, such as optionally substituted alkylene, alkyleneoxy, arylene, heteroalkylene, heteroalkyleneoxy, or —N($R^{N1}$)—, where $R^{N1}$ is H, optionally substituted alkyl, alkaryl, or aryl; and where one of $R^L$ and X can optionally combine to form an optionally substituted heterocyclyl.

In one instance, the composite or replica can be functionalized with one or more particles. Such particles may be useful for detection, drug delivery, etc. Exemplary particles include any described herein, including a nanoparticle (e.g., a nanotube), a microparticle, a quantum dot, a lipid particle, or a liposome, where each of these particles can optionally further include a label, a tag, a peptide, an antibody, a coating, a linker, and/or a drug, such as any described herein.

In another instance, the composite or replica can be functionalized with one or more coatings. Such coatings may be useful for biocompatibility and/or biodistribution profiles. Exemplary coatings include a hydrogel, a polyether (e.g., a polyethylene glycol or a polypropylene glycol), a polymer (e.g., an epoxy, a polyaniline), a dendrimer, a metal (e.g., a noble metal, such as gold, platinum, silver, etc.), an oxide coating (e.g., a zirconium oxide, a tin oxide, a zinc oxide, or a titanium oxide coating, including other dopants such as silicon, barium, manganese, iron, etc., such those coatings obtained by atomic layer deposition, hydrothermal conversion, sol-gel conversion, thermal annealing, and/or thermal evaporation), a ceramic (e.g., boron nitride), etc. In yet another instance, the composite or replica can be functionalized within a matrix, such as a polymeric matrix, a protein matrix, etc.

Composites and replicas can be readily converted to other types of materials. For instance, the silicon and oxygen atoms within the underlying silica structure can be displaced and/or replaced with other types of atoms (e.g., metallic atoms). In addition, the underlying organic matter provided by the biological sample can be removed or transformed (e.g., into conductive carbon). Such silica displacement reactions can be performed to obtain vast types of replicas, such as those including titanium oxide (e.g., titania (e.g., $TiO_2$) and titanate (e.g., $TiO_3$), including doped or complex forms thereof, such as $M_2TiO_4$ or $MTiO_3$, where M is a metal, such as a divalent metal (e.g., Ba, Sr, or Mg), magnesium oxide (e.g., MgO, as well as doped and complex forms thereof, such as $MgO/MTiO_3$). These displacement reactions are generally conducted in the presence of a reactant (a halide gas or an elemental gas), which results in oxidation/reduction or metathesis reactions to effectively displace or replace a silica or oxygen atom (of the composite or replica) with an atom from the reactant. After the displacement reaction, further reactions can be conducted to etch certain elements, coat the composite/replica, etc. to obtain further functionality.

EXAMPLES

Example 1: Hydrogel Particles Derived from Living Cells

The demand to create precision 3D soft materials is increasingly important for burgeoning applications such as flexible electronics, soft robotics, and tissue engineering. Often materials are needed at scales that enable relatively straightforward manufacturing approaches using extrusion, roll-to-roll, casting/spin coating, molding, and 3D printing. For complex 3D shapes, the manufacturing challenge increases as dimensions scale down, for example, to the size of micro and nano-particles. Thus, there has been considerable attention aimed at developing strategies for synthesis of complex or otherwise non-spherical soft colloidal particles.

Noteworthy approaches include emulsion-based techniques, microfluidic techniques, methods based on flow (photo) lithography, and particle replication in a non-wetting template (PRINT) method. However, these methods do not yet approach the structural complexity found in living systems such as single cells and multicellular organisms. In particular, abilities to synthetically replicate the complexity of animal cell morphology, in and range of both hard and soft materials would enable numerous areas of materials science and medicine.

Recently, we have developed a process to generate biocomposites and inorganic replicas of biological cells and soft tissues (see, e.g., Kaehr B et al., "Cellular complexity captured in durable silica biocomposites," *Proc. Nat'l Acad. Sci. USA* 2012; 109(43):17336-41; Townson J L et al., "Synthetic fossilization of soft biological tissues and their shape-preserving transformation into silica or electron-conductive replicas," *Nat. Commun.* 2014; 5:5665 (8 pp.); Meyer K C et al., "Mechanically encoded cellular shapes for synthesis of anisotropic mesoporous particles," *J. Am. Chem. Soc.* 2014; 136:13138-41; and Lou Y R et al., "Silica bioreplication preserves three-dimensional spheroid structures of human pluripotent stem cells and HepG2 cells," *Sci. Rep.* 2015; 5:13635 (9 pp.)). Briefly, external and internal bio-surfaces are replicated in nanometer thick, conformal silica layers using a solution-based, sol gel process. Removal of the biological template via high temperature calcination results in a shape-preserved silica cell replica (SCR) with mesoporosity. Building upon this approach, we surmised that this shape-preserved porous silica could serve as a suitable scaffold for subsequent templating of soft, synthetic polymers. Here, we describe the synthesis of all polymer replicas of mammalian biological cells. This provides a foundation to develop particles with nearly limitless architectural complexity derived from dynamic biological templates.

Porous silica replicas of cells were prepared as follows. Briefly, fixed cells were incubated in a dilute silicic acid solution for about 12-16 hrs at about 40° C. and subsequently rinsed. Next, the organic template can be removed via calcination at relatively high temperature (500° C.); however, we found that removal of the organic template via acid digestion (e.g., with HNO₃ or HF acid) led to more consistent polymer replication, for example, using red blood cell templates. Using acid digestion, drying was not required.

Following removal of the organics and considering the electrostatic characteristics of the porous silica particles (e.g., between −10 mV to 20 mV), we initially attempted to adsorb low molecular weight cationic polymer (polyethylenimine; PEI) to be subsequently polymerized using a bifunctional crosslinker. Polymerized silica replicas (i.e., a construct including silica nanolayers and polymer layers) could be formed. Upon etching of the silica, however, no particles were recovered indicating insufficient templating and/or crosslinking.

Figure 3A:
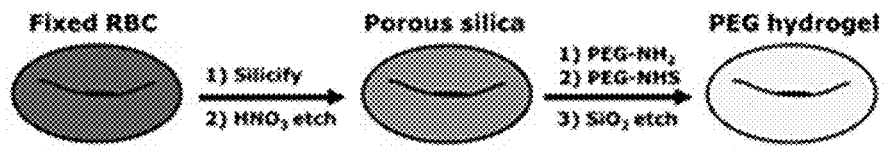
FIG. 3A-3C shows bioreplication of biological cells in poly(ethylene glycol) (PEG). Provided are a schematic showing a silification and polymerization process using red blood cells (FIG. 3A); an optical microphotograph of RBC-templated PEG constructs (e.g., replicas or composites) (FIG. 3B); and an optical microphotograph of HeLa cell-templated PEG constructs (FIG. 3C).

We also tested other polymers, including a first PEG precursor, e.g., an 8-arm polyethylene glycol (PEG) amine (PEG-NH$_2$). PEG-NH$_2$ was incubated with the template, rinsed, and subsequently incubated a second PEG precursor, e.g., an 8-arm 'crosslinking' PEG containing terminal NHS groups (PEG-NHS) (see, e.g., FIG. 3A). Etching of the silica (SiO$_2$ nanolayers) provided an all polymer replica (e.g., a PEG hydrogel replica, as shown in FIG. 3A).

Figure 3B:
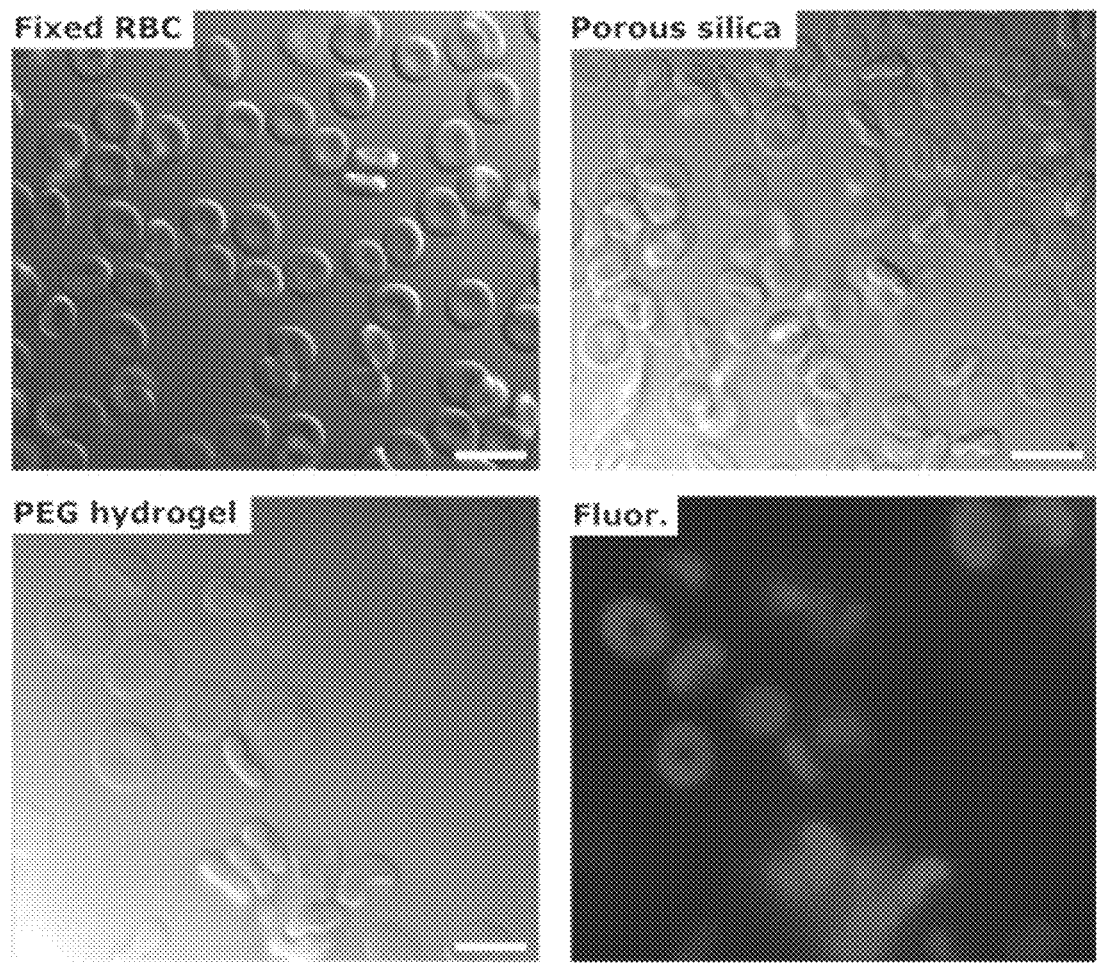
Figure 3C:
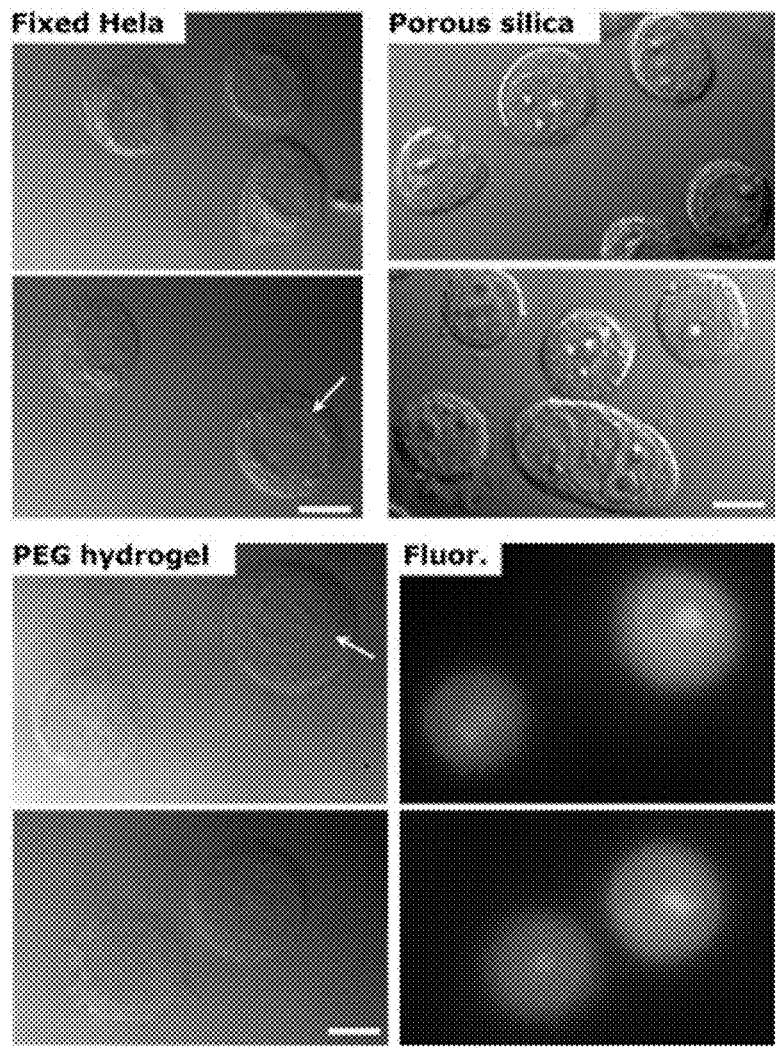
Figure 5:
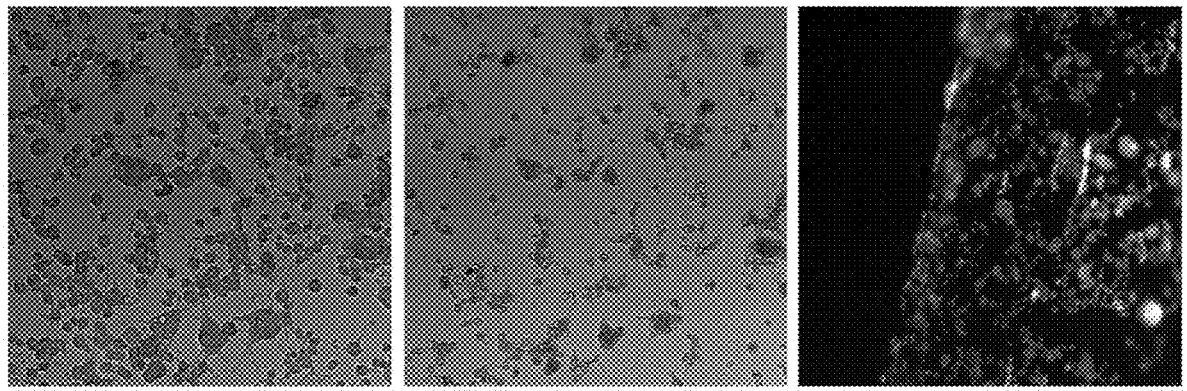
FIG. 5 shows polymeric replicas of interconnected neuron-like cells (NG-108). Provided are optical microphotographs of cells prior to etching of silica (left) and after etching of silica (center), as well as an image of an edge of a deformable free-standing film including interconnected cell replicas (right).

This method proved simple and effective for translating silica composites of red blood cells into all polymeric replicas (FIG. 3B) and for translating silica composites of Hela cells into all polymeric replicas (FIG. 3C). Remarkably, internal features of Hela, such as nuclear membranes and cytoplasmic bodies, appear replicated in the polymer replicas (see white arrows in FIG. 3C). Neuron-like NG108 cells were also employed as a template for forming a free-standing film (FIG. 5).

Figure 4A:
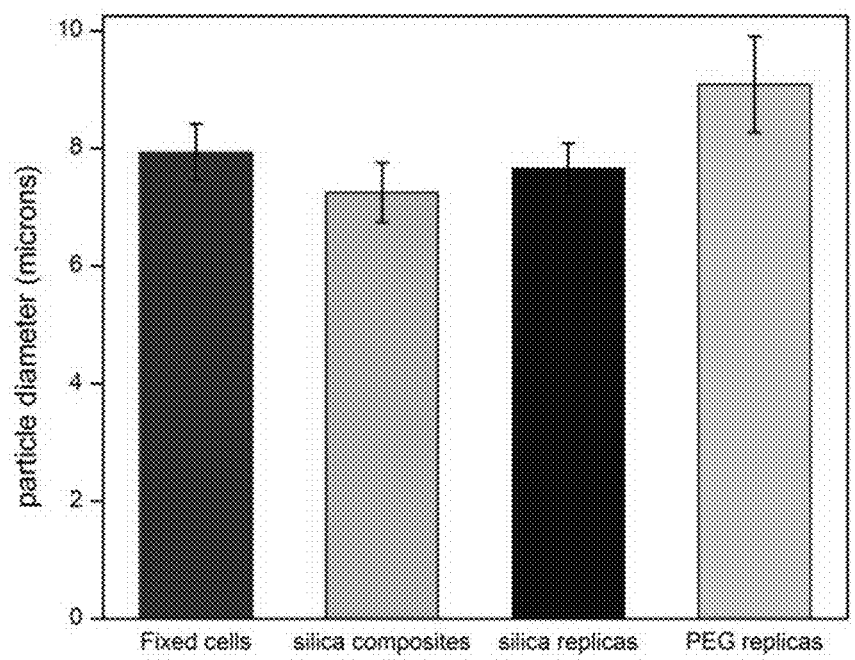
FIG. 4A-4B shows size changes and stiffness measurements for various constructs. Provided are a graph showing statistical comparison of particle size during the replication process, which shows minimal size changes (FIG. 4A) and another graph showing measurements of the particle modulus under varying degrees of cross-linking, which shows tenability across a range of a few kPas to 100s of kPas (FIG. 4B).
Figure 4B:
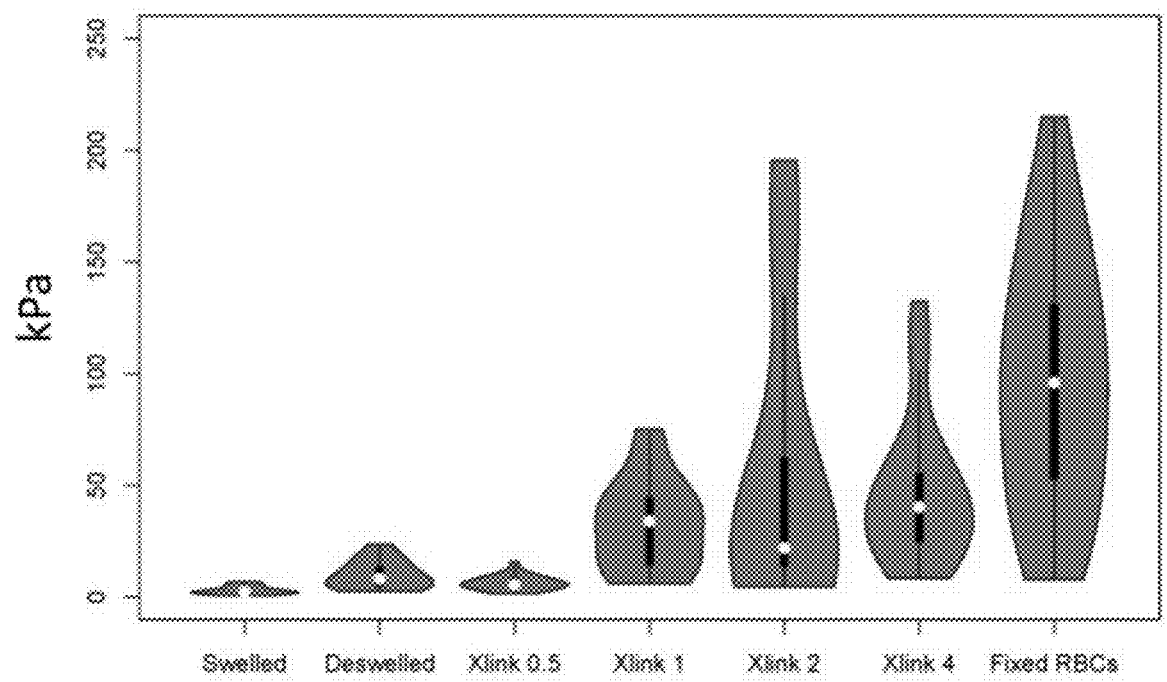

Furthermore, the physical characteristics of such composites and replicas can be controlled by the extent of crosslinking of the polymers and swelling of the resultant constructs (see, e.g., FIG. 4A-4B). Such control over the three-dimensional architecture of nano to microscale materials can provide useful physical characteristics, e.g., such as those displayed in nanoscale rods and wires.

Example 2: Diagnostic and Therapeutic Cellular Vehicles

The constructs herein can be useful in the development of artificial red blood cells for mitigation of trauma scenarios, therapeutic delivery and defense, and as a potential carrier for advanced in vivo sensors (e.g., biometrics). To these ends, we can adapt silica replicas as templates providing cellular structures and functions and modify the replica to provide synthetic constructs having useful hard/soft chemistries.

The development of an effective blood substitute has been a decades long—and largely unsuccessful—scientific challenge. The requirements for artificial blood include mimicry or improvement of the oxygen carrying capacity and volume of whole blood. Such artificial blood substitutes should be formed from non-immunogenic materials, preferably with long (e.g., room temperature) shelf-life beyond donated blood, which has an estimated shelf life of 42 days when refrigerated. Three strategies have evolved to meet this need. Crosslinked hemoglobins, perfluorocarbons oxygen carriers, and the emerging field of non-immunogenic blood that is derived from stem cells. All approaches suffer from a myriad of potentially insurmountable issue, including immunogenic reactions, high toxicity (e.g., NO scavenging by hemoglobins) and inability to scale (stem cells).

We hypothesize for a blood substitute to be effective, it must mimic the salient features of a natural cell (e.g., shape and mechanical properties, osmoregulatory functions and payload capacity) using materials that do not elicit an immunogenic response. We have recently pioneered a process to generate near exact red blood cell (RBC) mimics with non-immunogenic materials. This advance provides the foundation to realize an effective blood substitute, develops a multifunctional carrier for defense and therapeutic delivery, and provides a universal foundation for synthetic, artificial cells.

The ideal mechanical and transport properties of natural RBCs are a consequence of its evolutionarily-honed asymmetric shape. A foundation of our approach is our recent breakthrough ability to synthesize an exact polymeric replica of an RBC. Briefly, RBCs are subjected to a silica bioreplication process and thermally calcined to render a mesoporous silica replica (see, e.g., Meyer K C et al., "Mechanically encoded cellular shapes for synthesis of anisotropic mesoporous particles," *J. Am. Chem. Soc.* 2014; 136:13138-41). Infiltration and crosslinking of poly(ethylene glycol; PEG) precursors and removal of the silica template results in a shape-preserved polymeric replica with RBC-like deformability and hydration properties.

Figure 6A:
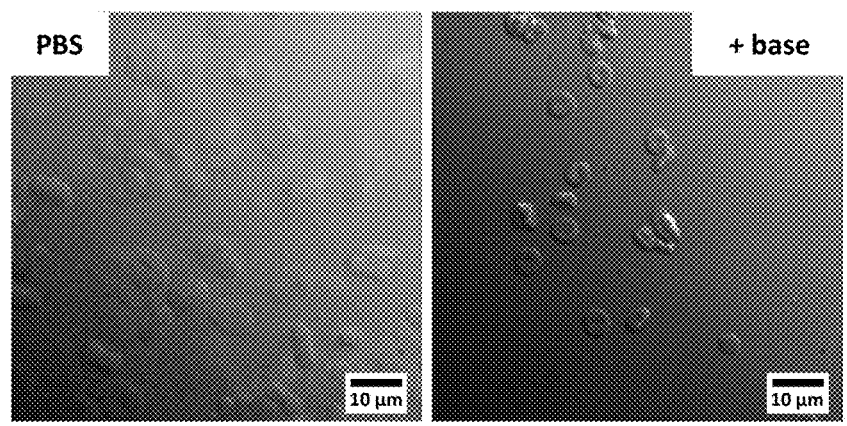
FIG. 6A-6B shows constructs that can be designed to swell or shrink in response to environmental perturbations. Provided are optical microphotographs of constructs in the presence of a buffer (PBS, left) or in the presence of a base (right) (FIG. 6A), and other exemplary optical microphotographs of constructs in the presence of a buffer (PBS, left) or in the presence of a base (right) (FIG. 6B).
Figure 6B:
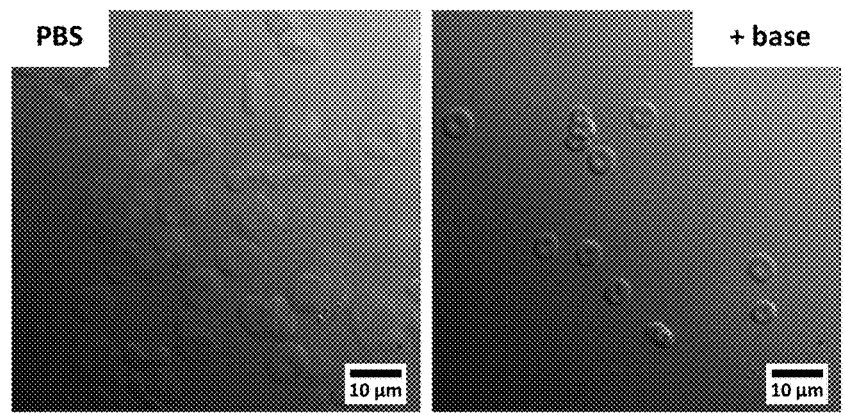
Figure 7:
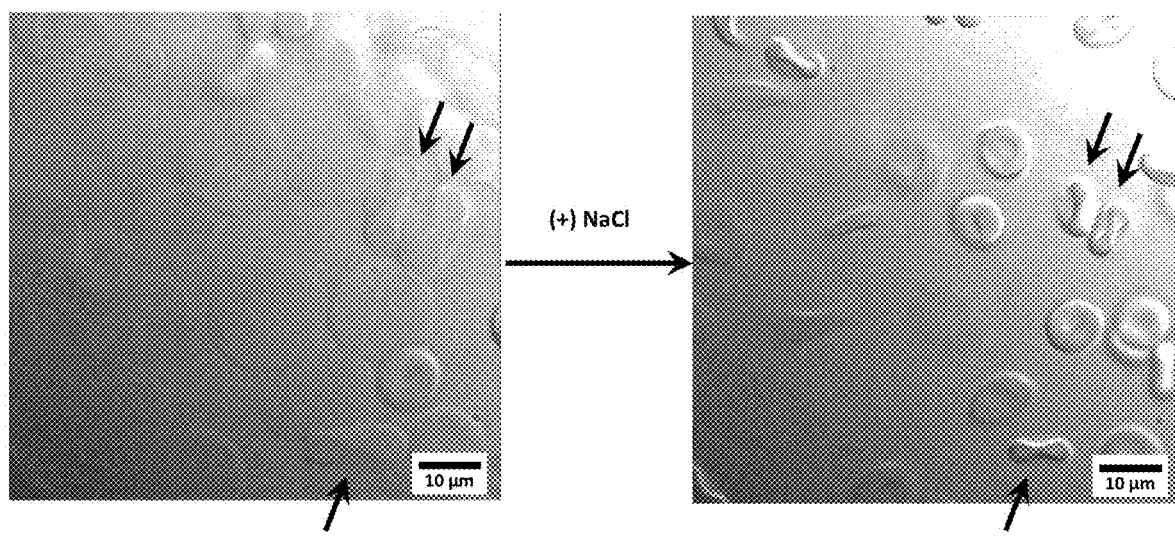
FIG. 7 shows constructs that are responsive to ionic strength, in which the construct includes a protein/PEG hybrid hydrogel with endogenous cross-linked hemoglobin (e.g., by avoiding the acid digestion step). Provided are optical microphotographs of constructs under a lower ionic strength condition (left) and under a higher ionic strength condition (right).

FIGS. 6A-6B and FIG. 7 provide polymeric replicas having the general shape of an RBC. As can be seen, the replica can be designed to swell or shrink in response to environmental perturbations, including the presence of a base (FIG. 6A-6B) or a change in ionic strength (FIG. 7).

Such polymeric replicas can be further optimized. In one instance, perfluorodecalin (PFD) loaded particles can be developed to enhance oxygen-carrying capacity. PFD is used as a blood substitute (FDA-approved Fluosol) due to its high oxygen carrying capacity (~33% by volume) and low toxicity. However, stable emulsification of the fluorocarbon in water has proven difficult, leading to poor shelf-life and, ultimately, withdrawal of Fluosol from market in 1994. Thus, also described herein is a polymeric RBC loaded with PFD, which would represent a stabilized and durable emulsion. Loading can be achieved by evacuation of the RBC mimic followed by resolution with PFD. O$_2$-carrying capacity and release can be evaluated using O$_2$ saturation versus pressure analysis in bulk and microfluidic (capillary-like) environments to assess material properties (modulus, leakage) with single-particle resolution.

Initially, PEG-based polymers can be employed for the construct. Alternatives to PEG for particle immuno-cloaking using biodegradable (polyamino acids) and non-biodegradable (polyglycerol, vinyl polymers). In addition, further oxygen carriers (e.g., hemoglobins and/or porphyrins) can be incorporated into the construct. Further modifications include use of a lipid layer to encapsulate the construct (e.g., to improve non-immunogenicity and/or to reduce PFD leakage), thereby providing a biocompatible, oxygen-permeable thin film. Development of a long-circulating RBC-like carrier could enable cloaking/interfacing of micro-electronic vectors for next generation biometrics for health monitoring, battlefield trauma, and trust assurance (see, e.g., Chen L Y et al., "Mass fabrication and delivery of 3D multilayer µTags into living cells," *Sci. Rep.* 2013; 3:2295 (6 pp.)).

Such RBC mimics can be engineered to facilitate processing and/or purification prior to or after use. For instance, particles can be engineered for active withdrawal (e.g., under dialysis) using a particle (e.g., magnetic nanoparticles) or binding groups (e.g., biorthogonal chemistries, such as azide-alkyne or other "click" chemistries). Various physicochemical aspects can be optimized, e.g., using in vitro experiments complemented with computational studies of solvation/desolvation dynamics, cargo uptake and leakage, and/or mechanical properties.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A synthetic construct comprising:
   a polymeric replica of a biological sample, wherein the replica comprises a shape-preserved layer comprising a polymeric precursor or a polymer, wherein the polymer or the polymeric precursor comprises a poly(ethylene glycol) group, an amino acid, a glycerol group, and/or a vinyl group, or polyelectrolyte pairs comprising alternating charge within the layer-by-layer assembly;
   an oxygen carrier loaded within the polymeric replica; and
   optionally, one or more endogenous or exogenous oxygen-binding molecules loaded within the polymeric replica.

2. The construct of claim 1, further comprising:
   a lipid layer coating surrounding a periphery of the construct.

3. The construct of claim 1, further comprising:
   a particle or a reactive group disposed within the construct or on a surface of the construct.

4. The construct of claim 1, wherein the biological sample comprises a red blood cell.

5. The construct of claim 1, wherein the oxygen carrier comprises a perfluorinated group or an emulsion thereof.

6. The construct of claim 1, wherein at least one of the one or more endogenous or exogenous oxygen-binding molecules comprises hemoglobin, porphyrin, heme protein, hemerythrin, hemocyanin, methemoglobin, or a modified form, a cross-linked form, a polymerized form, a conjugated form, and/or a recombinant form thereof.

7. The construct of claim 1, further comprising:
   a stabilizer, an antibiotic, a vitamin, a nutrient, a volume expander, and/or a salt disposed on a surface of the construct and/or disposed within a solution comprising the construct.

8. A synthetic construct comprising:
   a polymeric replica of a biological sample, wherein the replica consists essentially of a polymeric precursor or a polymer;
   an oxygen carrier loaded within the polymeric replica; and
   one or more endogenous or exogenous oxygen-binding molecules loaded within the polymeric replica, wherein at least one of the one or more endogenous or exogenous oxygen-binding molecules comprises hemoglobin, porphyrin, heme protein, hemerythrin, hemocyanin, methemoglobin, or a modified form, a cross-linked form, a polymerized form, a conjugated form, and/or a recombinant form thereof.

9. The construct of claim 8, further comprising:
   a lipid layer coating surrounding a periphery of the construct.

10. The construct of claim 8, further comprising:
    a particle or a reactive group disposed within the construct or on a surface of the construct.

11. The construct of claim 8, wherein the polymer or the polymeric precursor comprises a poly(ethylene glycol) group, an amino acid, a glycerol group, and/or a vinyl group.

12. The construct of claim 8, wherein the polymer or the polymeric precursor comprises polyelectrolyte pairs comprising alternating charge within the layer-by-layer assembly.

13. The construct of claim 8, wherein the biological sample comprises a red blood cell.

14. The construct of claim 8, wherein the oxygen carrier comprises a perfluorinated group or an emulsion thereof.

15. The construct of claim 8, further comprising:
    a stabilizer, an antibiotic, a vitamin, a nutrient, a volume expander, and/or a salt disposed on a surface of the construct and/or disposed within a solution comprising the construct.

* * * * *